(12) United States Patent
Meyer et al.

(10) Patent No.: US 10,420,872 B2
(45) Date of Patent: Sep. 24, 2019

(54) DEGASSING SYSTEM FOR DIALYSIS

(71) Applicant: Medtronic, Inc., Minneapolis, MN (US)

(72) Inventors: Thomas E. Meyer, Stillwater, MN (US); William P. Hajko, Safety Harbor, FL (US); Daniel Jordan Bloomberg, Minneapolis, MN (US)

(73) Assignee: Medtronic, Inc., Minneapolis, MN (US)

(*) Notice: Subject to any disclaimer, the term of this patent is extended or adjusted under 35 U.S.C. 154(b) by 144 days.

(21) Appl. No.: 15/618,187

(22) Filed: Jun. 9, 2017

(65) Prior Publication Data

US 2017/0274129 A1    Sep. 28, 2017

Related U.S. Application Data

(63) Continuation of application No. 14/566,686, filed on Dec. 10, 2014, now Pat. No. 9,713,665.

(51) Int. Cl.
*A61M 1/16* (2006.01)
*B01D 19/00* (2006.01)

(52) U.S. Cl.
CPC ....... *A61M 1/1658* (2013.01); *B01D 19/0036* (2013.01); *B01D 19/0047* (2013.01); *B01D 19/0063* (2013.01); *B01D 19/0068* (2013.01); *A61M 1/1696* (2013.01); *A61M 2202/0225* (2013.01); *A61M 2205/3382* (2013.01); *A61M 2205/3386* (2013.01)

(58) Field of Classification Search
CPC ............ B01D 19/0031; B01D 19/0036; B01D 19/0047; B01D 19/0063; B01D 19/0068; A61M 1/1658; A61M 1/1696
See application file for complete search history.

(56) References Cited

U.S. PATENT DOCUMENTS

| | | |
|---|---|---|
| 3,091,098 A | 5/1963 | Bowers |
| 3,370,710 A | 2/1968 | Bluemle |
| 3,506,126 A | 4/1970 | Lindsay, Jr. |
| 3,608,729 A | 9/1971 | Haselden |

(Continued)

FOREIGN PATENT DOCUMENTS

| | | |
|---|---|---|
| CN | 101687070 | 3/2010 |
| CN | 101883594 A | 11/2010 |

(Continued)

OTHER PUBLICATIONS

U.S. Appl. No. 13/424,454.

(Continued)

*Primary Examiner* — Jason M Greene
(74) *Attorney, Agent, or Firm* — Kenneth Collier; Roger Hahn

(57) ABSTRACT

The degassing system can include a degassing vessel and can utilize a vacuum pump and a fluid pump located downstream of the degassing vessel to control the pressure within the degassing vessel in order to control the concentration of gases in fluid exiting the degassing system. The degassing system can further comprise sensors in communication with the pumps to control the rate of flow and pressure through the degassing system. The degassing system may be placed in a dialysate flow path to remove dissolved gases including carbon dioxide from the dialysate.

15 Claims, 12 Drawing Sheets

(56) References Cited

U.S. PATENT DOCUMENTS

| | | | |
|---|---|---|---|
| 3,669,878 A | 6/1972 | Marantz | |
| 3,669,880 A | 6/1972 | Marantz | |
| 3,692,648 A | 9/1972 | Matloff | |
| 3,776,819 A | 12/1973 | Williams | |
| 3,809,241 A | 5/1974 | Alvine | |
| 3,850,835 A | 11/1974 | Marantz | |
| 3,884,808 A | 5/1975 | Scott | |
| 3,902,490 A | 9/1975 | Jacobsen | |
| 3,932,150 A | 1/1976 | Komai | |
| 3,939,069 A | 2/1976 | Granger | |
| 3,989,622 A | 11/1976 | Marantz | |
| 4,060,485 A | 11/1977 | Eaton | |
| 4,094,775 A | 6/1978 | Mueller | |
| 4,136,708 A | 1/1979 | Cosentino | |
| 4,142,845 A | 3/1979 | Lepp | |
| 4,201,555 A | 5/1980 | Tkach | |
| 4,209,392 A | 6/1980 | Wallace | |
| 4,269,708 A | 5/1981 | Bonomini | |
| 4,316,725 A | 2/1982 | Hovind | |
| 4,371,385 A | 2/1983 | Johnson | |
| 4,374,382 A | 2/1983 | Markowitz | |
| 4,376,707 A | 3/1983 | Lehmann | |
| 4,381,999 A | 5/1983 | Boucher | |
| 4,430,098 A | 2/1984 | Bowman | |
| 4,460,555 A | 7/1984 | Thompson | |
| 4,490,135 A | 12/1984 | Troutner | |
| 4,556,063 A | 12/1985 | Thompson | |
| 4,562,751 A | 1/1986 | Nason | |
| 4,581,141 A | 4/1986 | Ash | |
| 4,612,122 A | 9/1986 | Ambrus | |
| 4,650,587 A | 3/1987 | Polak | |
| 4,678,408 A | 7/1987 | Mason | |
| 4,685,903 A | 8/1987 | Cable | |
| 4,695,385 A | 9/1987 | Boag | |
| 4,715,398 A * | 12/1987 | Shouldice | A61M 1/1658 137/171 |
| 4,739,492 A * | 4/1988 | Cochran | A61M 1/1656 210/321.71 |
| 4,747,822 A | 5/1988 | Peabody | |
| 4,750,494 A | 6/1988 | King | |
| 4,816,162 A | 3/1989 | Rosskopf et al. | |
| 4,826,663 A | 5/1989 | Alberti | |
| 4,828,693 A | 5/1989 | Lindsay | |
| 4,885,001 A | 12/1989 | Leppert | |
| 4,900,308 A | 2/1990 | Verkaart | |
| 4,915,713 A | 4/1990 | Buzza | |
| 4,950,230 A | 8/1990 | Kendell | |
| 4,977,888 A | 12/1990 | Rietter | |
| 5,015,388 A | 5/1991 | Pusineri | |
| 5,032,265 A | 7/1991 | Jha | |
| 5,080,653 A | 1/1992 | Voss | |
| 5,092,886 A | 3/1992 | Dobos-Hardy | |
| 5,097,122 A | 3/1992 | Coiman | |
| 5,114,580 A | 5/1992 | Ahmad | |
| 5,127,404 A | 7/1992 | Wyborny | |
| 5,141,493 A | 8/1992 | Jacobsen | |
| 5,180,403 A * | 1/1993 | Kogure | B01D 19/0005 95/265 |
| 5,192,132 A | 3/1993 | Pelensky | |
| 5,203,890 A | 4/1993 | Tatsuo | |
| 5,230,702 A | 7/1993 | Lindsay | |
| 5,284,470 A | 2/1994 | Beltz | |
| 5,302,288 A | 4/1994 | Meidl | |
| 5,305,745 A | 4/1994 | Zacouto | |
| 5,308,315 A | 5/1994 | Khuri | |
| 5,318,750 A | 6/1994 | Lascombes | |
| 5,399,157 A | 3/1995 | Goux | |
| 5,419,347 A | 5/1995 | Carruth | |
| 5,441,049 A | 8/1995 | Masano | |
| 5,442,969 A | 8/1995 | Troutner | |
| 5,468,388 A | 11/1995 | Goddard et al. | |
| 5,507,723 A | 4/1996 | Keshaviah | |
| 5,591,344 A | 1/1997 | Kenley | |
| 5,643,201 A | 7/1997 | Peabody | |
| 5,662,806 A | 9/1997 | Keshaviah et al. | |
| 5,683,432 A | 11/1997 | Goedeke | |
| 5,685,835 A | 11/1997 | Brugger | |
| 5,685,988 A | 11/1997 | Malchesky | |
| 5,702,536 A | 12/1997 | Carruth | |
| 5,744,031 A | 4/1998 | Bene | |
| 5,762,782 A | 6/1998 | Kenley | |
| 5,849,179 A | 12/1998 | Emerson | |
| 5,858,186 A | 1/1999 | Glass | |
| 5,863,421 A | 1/1999 | Peter | |
| 5,938,938 A | 8/1999 | Bosetto | |
| 5,944,684 A | 8/1999 | Roberts | |
| 5,948,251 A | 9/1999 | Brugger | |
| 6,048,732 A | 4/2000 | Anslyn | |
| 6,052,622 A | 4/2000 | Holmstrom | |
| 6,058,331 A | 5/2000 | King | |
| 6,114,176 A | 9/2000 | Edgson et al. | |
| 6,126,831 A | 10/2000 | Goldau | |
| 6,171,480 B1 | 1/2001 | Lee | |
| 6,230,059 B1 | 5/2001 | Duffin | |
| 6,248,093 B1 | 6/2001 | Moberg | |
| 6,251,167 B1 * | 6/2001 | Berson | B01D 19/0005 210/188 |
| 6,254,567 B1 | 7/2001 | Treu | |
| 6,264,680 B1 | 7/2001 | Ash | |
| 6,321,101 B1 | 11/2001 | Holmstrom | |
| 6,362,591 B1 | 3/2002 | Moberg | |
| 6,363,279 B1 | 3/2002 | Ben-Haim | |
| 6,521,184 B1 | 2/2003 | Edgson et al. | |
| 6,554,798 B1 | 4/2003 | Mann | |
| 6,555,986 B2 | 4/2003 | Moberg | |
| 6,589,229 B1 | 7/2003 | Connelly | |
| 6,593,747 B2 | 7/2003 | Puskas | |
| 6,602,399 B1 | 8/2003 | Fromherz | |
| 6,627,164 B1 | 9/2003 | Wong | |
| 6,666,840 B1 | 12/2003 | Falkvall et al. | |
| 6,676,608 B1 | 1/2004 | Keren | |
| 6,711,439 B1 | 3/2004 | Bradley | |
| 6,719,745 B1 | 4/2004 | Taylor | |
| 6,726,647 B1 | 4/2004 | Sternby | |
| 6,780,322 B1 | 8/2004 | Bissler | |
| 6,814,724 B2 | 11/2004 | Taylor | |
| 6,818,196 B2 | 11/2004 | Wong | |
| 6,824,524 B1 | 11/2004 | Favre | |
| 6,861,266 B1 | 3/2005 | Sternby | |
| 6,878,283 B2 | 4/2005 | Thompson | |
| 6,960,179 B2 | 11/2005 | Gura | |
| 7,023,359 B2 | 4/2006 | Goetz | |
| 7,033,498 B2 | 4/2006 | Wong | |
| 7,074,332 B2 | 7/2006 | Summerton | |
| 7,077,819 B1 | 7/2006 | Goldau | |
| 7,097,630 B2 | 8/2006 | Gotch | |
| 7,101,519 B2 | 9/2006 | Wong | |
| 7,153,693 B2 | 12/2006 | Tajiri | |
| 7,169,303 B2 | 1/2007 | Sullivan | |
| 7,208,092 B2 | 4/2007 | Micheli | |
| 7,241,272 B2 | 7/2007 | Karoor | |
| 7,276,042 B2 | 10/2007 | Polaschegg | |
| 7,279,031 B1 | 10/2007 | Wright | |
| 7,318,892 B2 | 1/2008 | Connell | |
| 7,326,576 B2 | 2/2008 | Womble et al. | |
| 7,435,342 B2 | 10/2008 | Tsukamoto | |
| 7,488,447 B2 | 2/2009 | Sternby | |
| 7,500,958 B2 | 3/2009 | Asbrink | |
| 7,537,688 B2 | 5/2009 | Tarumi | |
| 7,544,300 B2 | 6/2009 | Brugger | |
| 7,544,737 B2 | 6/2009 | Poss | |
| 7,563,240 B2 | 7/2009 | Gross | |
| 7,566,432 B2 | 7/2009 | Wong | |
| 7,575,564 B2 | 8/2009 | Childers | |
| 7,597,806 B2 | 10/2009 | Uchi | |
| 7,674,231 B2 | 3/2010 | McCombie | |
| 7,704,361 B2 | 4/2010 | Garde | |
| 7,736,507 B2 | 6/2010 | Wong | |
| 7,744,553 B2 | 6/2010 | Kelly | |
| 7,754,852 B2 | 7/2010 | Burnett | |
| 7,756,572 B1 | 7/2010 | Fard | |
| 7,776,210 B2 | 8/2010 | Rosenbaum | |
| 7,785,463 B2 | 8/2010 | Bissler | |
| 7,790,103 B2 | 9/2010 | Shah | |

(56) References Cited

U.S. PATENT DOCUMENTS

| | | |
|---|---|---|
| 7,794,141 B2 | 9/2010 | Perry |
| 7,794,419 B2 | 9/2010 | Paolini |
| 7,850,635 B2 | 12/2010 | Polaschegg |
| 7,857,976 B2 | 12/2010 | Bissler |
| 7,867,214 B2 | 1/2011 | Childers |
| 7,896,831 B2 | 3/2011 | Sternby |
| 7,922,686 B2 | 4/2011 | Childers |
| 7,922,911 B2 | 4/2011 | Micheli |
| 7,947,179 B2 | 5/2011 | Rosenbaum |
| 7,955,290 B2 | 6/2011 | Karoor |
| 7,955,291 B2 | 6/2011 | Sternby |
| 7,967,022 B2 | 6/2011 | Grant |
| 7,981,082 B2 | 7/2011 | Wang |
| 7,988,854 B2 | 8/2011 | Tsukamoto |
| 8,002,726 B2 | 8/2011 | Karoor |
| 8,029,454 B2 | 10/2011 | Kelly |
| 8,034,161 B2 | 10/2011 | Gura |
| 8,066,658 B2 | 11/2011 | Karoor |
| 8,070,709 B2 | 12/2011 | Childers |
| 8,080,161 B2 | 12/2011 | Ding et al. |
| 8,087,303 B2 | 1/2012 | Beavis |
| 8,096,969 B2 | 1/2012 | Roberts |
| 8,180,574 B2 | 5/2012 | Lo |
| 8,183,046 B2 | 5/2012 | Lu |
| 8,187,250 B2 | 5/2012 | Roberts |
| 8,197,439 B2 | 6/2012 | Wang |
| 8,202,241 B2 | 6/2012 | Karakama |
| 8,246,826 B2 | 8/2012 | Wilt |
| 8,273,049 B2 | 9/2012 | Demers |
| 8,292,594 B2 | 10/2012 | Tracey |
| 8,303,532 B2 | 11/2012 | Hamada |
| 8,313,642 B2 | 11/2012 | Yu |
| 8,317,492 B2 | 11/2012 | Demers |
| 8,357,113 B2 | 1/2013 | Childers |
| 8,366,316 B2 | 2/2013 | Kamen |
| 8,366,655 B2 | 2/2013 | Kamen |
| 8,404,491 B2 | 3/2013 | Li |
| 8,409,441 B2 | 4/2013 | Wilt |
| 8,409,444 B2 | 4/2013 | Wong |
| 8,449,487 B2 * | 5/2013 | Hovland ............... A61M 1/166 604/4.01 |
| 8,491,517 B2 | 7/2013 | Karoor |
| 8,496,809 B2 | 7/2013 | Roger |
| 8,499,780 B2 | 8/2013 | Wilt |
| 8,500,672 B2 | 8/2013 | Caleffi |
| 8,500,676 B2 | 8/2013 | Jansson |
| 8,500,994 B2 | 8/2013 | Weaver |
| 8,512,271 B2 | 8/2013 | Moissl |
| 8,518,258 B2 | 8/2013 | Balschat |
| 8,518,260 B2 | 8/2013 | Raimann |
| 8,521,482 B2 | 8/2013 | Akonur |
| 8,535,525 B2 | 9/2013 | Heyes |
| 8,560,510 B2 | 10/2013 | Brueggerhoff |
| 8,562,822 B2 | 10/2013 | Roger |
| 8,597,227 B2 | 12/2013 | Childers |
| 8,696,626 B2 | 4/2014 | Kirsch |
| 8,777,892 B2 | 7/2014 | Sandford |
| 8,903,492 B2 | 12/2014 | Soykan |
| 8,906,240 B2 | 12/2014 | Crnkovich |
| 9,144,640 B2 | 9/2015 | Pudil |
| 9,173,987 B2 | 11/2015 | Meyer |
| 2002/0027106 A1 | 3/2002 | Smith |
| 2002/0042561 A1 | 4/2002 | Schulman |
| 2002/0045851 A1 | 4/2002 | Suzuki |
| 2002/0104800 A1 | 8/2002 | Collins |
| 2002/0112609 A1 | 8/2002 | Wong |
| 2003/0010717 A1 | 1/2003 | Brugger |
| 2003/0034305 A1 | 2/2003 | Luehmann |
| 2003/0080059 A1 | 5/2003 | Peterson |
| 2003/0097086 A1 | 5/2003 | Gura |
| 2003/0105424 A1 | 6/2003 | Karoor |
| 2003/0105435 A1 | 6/2003 | Taylor |
| 2003/0114787 A1 | 6/2003 | Gura |
| 2004/0019312 A1 | 1/2004 | Childers |
| 2004/0019320 A1 | 1/2004 | Childers |
| 2004/0068219 A1 | 4/2004 | Summerton |
| 2004/0082903 A1 | 4/2004 | Micheli |
| 2004/0099593 A1 | 5/2004 | DePaolis |
| 2004/0102732 A1 | 5/2004 | Naghavi |
| 2004/0143173 A1 | 7/2004 | Reghabi |
| 2004/0147900 A1 | 7/2004 | Polaschegg |
| 2004/0168969 A1 | 9/2004 | Sternby |
| 2004/0215090 A1 | 10/2004 | Erkkila |
| 2005/0006296 A1 | 1/2005 | Sullivan |
| 2005/0065760 A1 | 3/2005 | Murtfeldt |
| 2005/0101901 A1 | 5/2005 | Gura |
| 2005/0113796 A1 | 5/2005 | Taylor |
| 2005/0115898 A1 | 6/2005 | Sternby |
| 2005/0126961 A1 | 6/2005 | Bissler |
| 2005/0131331 A1 | 6/2005 | Kelly |
| 2005/0153904 A1 | 6/2005 | Fager |
| 2005/0126998 A1 | 7/2005 | Childers |
| 2005/0148923 A1 | 7/2005 | Sternby |
| 2005/0150832 A1 | 7/2005 | Tsukamoto |
| 2005/0234381 A1 | 10/2005 | Niemetz |
| 2005/0274658 A1 | 12/2005 | Rosenbaum |
| 2006/0025661 A1 | 2/2006 | Sweeney |
| 2006/0217771 A1 | 2/2006 | Soykan |
| 2006/0054489 A1 | 3/2006 | Denes |
| 2006/0076295 A1 | 4/2006 | Leonard |
| 2006/0157335 A1 | 7/2006 | Levine |
| 2006/0157413 A1 | 7/2006 | Bene |
| 2006/0186044 A1 | 8/2006 | Nalesso |
| 2006/0195064 A1 | 8/2006 | Plahey |
| 2006/0226079 A1 | 10/2006 | Mori |
| 2006/0241709 A1 | 10/2006 | Soykan |
| 2006/0264894 A1 | 11/2006 | Moberg |
| 2007/0007208 A1 | 1/2007 | Brugger |
| 2007/0066928 A1 | 3/2007 | Lannoy |
| 2007/0072285 A1 | 3/2007 | Barringer |
| 2007/0138011 A1 | 6/2007 | Hofmann |
| 2007/0140916 A1 | 6/2007 | Spiss |
| 2007/0175827 A1 | 8/2007 | Wariar |
| 2007/0179431 A1 | 8/2007 | Roberts |
| 2007/0213653 A1 | 9/2007 | Childers |
| 2007/0213665 A1 | 9/2007 | Curtin |
| 2007/0215545 A1 | 9/2007 | Bissler |
| 2007/0243113 A1 | 10/2007 | DiLeo |
| 2007/0255250 A1 | 11/2007 | Moberg |
| 2008/0006570 A1 | 1/2008 | Gura |
| 2008/0015493 A1 | 1/2008 | Childers et al. |
| 2008/0021337 A1 | 1/2008 | Li |
| 2008/0051696 A1 | 2/2008 | Curtin |
| 2008/0053905 A9 | 3/2008 | Brugger |
| 2008/0067132 A1 | 3/2008 | Ross |
| 2008/0093276 A1 | 4/2008 | Roger |
| 2008/0154543 A1 | 6/2008 | Rajagopal |
| 2008/0215247 A1 | 9/2008 | Tonelli |
| 2008/0217245 A1 | 9/2008 | Rambod |
| 2008/0230473 A1 | 9/2008 | Herbst |
| 2008/0253427 A1 | 10/2008 | Kamen |
| 2009/0012450 A1 | 1/2009 | Shah |
| 2009/0020471 A1 | 1/2009 | Tsukamoto |
| 2009/0078636 A1 | 3/2009 | Uchi |
| 2009/0084199 A1 | 4/2009 | Wright |
| 2009/0084718 A1 | 4/2009 | Prisco |
| 2009/0084721 A1 | 4/2009 | Yardimci |
| 2009/0101549 A1 | 4/2009 | Kamen |
| 2009/0101552 A1 | 4/2009 | Fulkerson |
| 2009/0101577 A1 | 4/2009 | Fulkerson |
| 2009/0105629 A1 | 4/2009 | Grant |
| 2009/0107335 A1 | 4/2009 | Wilt |
| 2009/0124963 A1 | 5/2009 | Hogard |
| 2009/0127193 A1 | 5/2009 | Updyke |
| 2009/0131858 A1 | 5/2009 | Fissell |
| 2009/0159527 A1 | 6/2009 | Mickols |
| 2009/0171261 A1 | 7/2009 | Sternby |
| 2009/0173682 A1 | 7/2009 | Robinson |
| 2009/0182263 A1 | 7/2009 | Burbank |
| 2009/0187138 A1 | 7/2009 | Lundtveit |
| 2009/0216045 A1 | 8/2009 | Singh |
| 2009/0223539 A1 | 9/2009 | Gibbel |
| 2009/0275849 A1 | 11/2009 | Stewart |
| 2009/0275883 A1 | 11/2009 | Chapman |

(56) References Cited

U.S. PATENT DOCUMENTS

| | | |
|---|---|---|
| 2009/0281484 A1 | 11/2009 | Childers |
| 2009/0314063 A1 | 12/2009 | Sternby |
| 2010/0004588 A1 | 1/2010 | Yeh |
| 2010/0007838 A1 | 1/2010 | Fujimoto |
| 2010/0010429 A1 | 1/2010 | Childers |
| 2010/0022936 A1 | 1/2010 | Gura |
| 2010/0030151 A1 | 2/2010 | Kirsch |
| 2010/0042035 A1 | 2/2010 | Moissl |
| 2010/0051552 A1 | 3/2010 | Rohde |
| 2010/0078092 A1 | 4/2010 | Weilhoefer |
| 2010/0078381 A1 | 4/2010 | Merchant |
| 2010/0078387 A1 | 4/2010 | Wong |
| 2010/0084330 A1 | 4/2010 | Wong |
| 2010/0087771 A1 | 4/2010 | Karakama |
| 2010/0094158 A1 | 4/2010 | Solem |
| 2010/0100027 A1* | 4/2010 | Schilthuizen ....... A61M 1/1696 604/6.09 |
| 2010/0102190 A1 | 4/2010 | Zhu et al. |
| 2010/0106071 A1 | 4/2010 | Wallenborg |
| 2010/0114012 A1 | 5/2010 | Sandford |
| 2010/0130906 A1 | 5/2010 | Balschat |
| 2010/0137693 A1 | 6/2010 | Porras |
| 2010/0137782 A1 | 6/2010 | Jansson |
| 2010/0140149 A1 | 6/2010 | Fulkerson |
| 2010/0168546 A1 | 7/2010 | Kamath |
| 2010/0192686 A1 | 8/2010 | Kamen |
| 2010/0199670 A1 | 8/2010 | Robertson |
| 2010/0213127 A1 | 8/2010 | Castellarnau |
| 2010/0217180 A1 | 8/2010 | Akonur |
| 2010/0217181 A1 | 8/2010 | Roberts |
| 2010/0224492 A1 | 9/2010 | Ding |
| 2010/0234795 A1 | 9/2010 | Wallenas |
| 2010/0241045 A1 | 9/2010 | Kelly |
| 2010/0252490 A1 | 10/2010 | Fulkerson |
| 2010/0274171 A1 | 10/2010 | Caleffi |
| 2010/0282662 A1 | 11/2010 | Lee |
| 2010/0312172 A1 | 12/2010 | Hoffman |
| 2010/0312174 A1 | 12/2010 | Hoffman |
| 2010/0326911 A1 | 12/2010 | Rosenbaum |
| 2010/0327586 A1 | 12/2010 | Mardirossian |
| 2011/0009798 A1 | 1/2011 | Kelly |
| 2011/0048949 A1 | 3/2011 | Ding et al. |
| 2011/0066043 A1 | 3/2011 | Banet |
| 2011/0071465 A1 | 3/2011 | Wang |
| 2011/0077574 A1 | 3/2011 | Sigg |
| 2011/0079558 A1 | 4/2011 | Raimann |
| 2011/0087187 A1 | 4/2011 | Beck |
| 2011/0100909 A1 | 5/2011 | Stange |
| 2011/0105983 A1 | 5/2011 | Kelly |
| 2011/0106003 A1 | 5/2011 | Childers |
| 2011/0120930 A1 | 5/2011 | Mishkin |
| 2011/0120946 A1 | 5/2011 | Levin |
| 2011/0130666 A1 | 6/2011 | Dong |
| 2011/0132838 A1 | 6/2011 | Curtis |
| 2011/0144570 A1 | 6/2011 | Childers |
| 2011/0160637 A1 | 6/2011 | Beiriger |
| 2011/0163030 A1 | 7/2011 | Weaver |
| 2011/0163034 A1 | 7/2011 | Castellarnau |
| 2011/0168017 A1 | 7/2011 | Lamers |
| 2011/0184340 A1 | 7/2011 | Tan |
| 2011/0189048 A1 | 8/2011 | Curtis |
| 2011/0220562 A1 | 9/2011 | Beiriger |
| 2011/0247973 A1 | 10/2011 | Sargand |
| 2011/0272337 A1 | 11/2011 | Palmer |
| 2011/0284377 A1 | 11/2011 | Rohde |
| 2011/0297593 A1 | 12/2011 | Kelly |
| 2011/0315611 A1 | 12/2011 | Fulkerson |
| 2011/0315632 A1 | 12/2011 | Freije |
| 2012/0006762 A1 | 1/2012 | McCabe |
| 2012/0016228 A1 | 1/2012 | Kroh |
| 2012/0031825 A1 | 2/2012 | Gura |
| 2012/0083729 A1 | 4/2012 | Childers |
| 2012/0085707 A1 | 4/2012 | Beiriger |
| 2012/0092025 A1 | 4/2012 | Volker |
| 2012/0115248 A1 | 5/2012 | Ansyln |
| 2012/0199205 A1 | 8/2012 | Eyrard |
| 2012/0220528 A1 | 8/2012 | VanAntwerp |
| 2012/0220926 A1 | 8/2012 | Soykan |
| 2012/0248017 A1 | 10/2012 | Beiriger |
| 2012/0258545 A1 | 10/2012 | Ash |
| 2012/0258546 A1 | 10/2012 | Marran |
| 2012/0259276 A1 | 10/2012 | Childers |
| 2012/0273354 A1 | 11/2012 | Orhan |
| 2012/0273415 A1 | 11/2012 | Gerber |
| 2012/0273420 A1 | 11/2012 | Gerber |
| 2012/0277546 A1 | 11/2012 | Soykan |
| 2012/0277552 A1 | 11/2012 | Gerber |
| 2012/0277604 A1 | 11/2012 | Gerber |
| 2012/0277650 A1 | 11/2012 | Gerber |
| 2012/0277655 A1 | 11/2012 | Gerber |
| 2012/0277722 A1 | 11/2012 | Gerber |
| 2012/0302945 A1 | 11/2012 | Hedmann |
| 2013/0001165 A1 | 1/2013 | Pohlmeier |
| 2013/0015302 A1 | 1/2013 | Örter |
| 2013/0018301 A1 | 1/2013 | Weaver |
| 2013/0019994 A1 | 1/2013 | Schaer |
| 2013/0030356 A1 | 1/2013 | Ding |
| 2013/0037465 A1 | 2/2013 | Heyes |
| 2013/0062265 A1 | 3/2013 | Balschat |
| 2013/0193073 A1 | 8/2013 | Hogard |
| 2013/0199998 A1 | 8/2013 | Kelly |
| 2013/0211730 A1 | 8/2013 | Wolff |
| 2013/0213890 A1 | 8/2013 | Kelly |
| 2013/0228516 A1 | 9/2013 | Jonsson |
| 2013/0228517 A1 | 9/2013 | Roger |
| 2013/0231607 A1 | 9/2013 | Roger |
| 2013/0248426 A1 | 9/2013 | Pouchoulin |
| 2013/0256227 A1 | 10/2013 | Kelly |
| 2013/0274642 A1 | 10/2013 | Soykan |
| 2013/0304020 A1 | 11/2013 | Wilt |
| 2013/0324915 A1 | 12/2013 | (Krensky)Britton |
| 2013/0330208 A1 | 12/2013 | Ly |
| 2013/0331774 A1 | 12/2013 | Farrell |
| 2014/0001112 A1 | 1/2014 | Karoor |
| 2014/0018727 A1 | 1/2014 | Burbank |
| 2014/0018728 A1 | 1/2014 | Plahey |
| 2014/0042092 A1 | 2/2014 | Akonur |
| 2014/0065950 A1 | 3/2014 | Mendelsohn |
| 2014/0088442 A1 | 3/2014 | Soykan |
| 2014/0110340 A1 | 4/2014 | White |
| 2014/0110341 A1 | 4/2014 | White |
| 2014/0158538 A1 | 6/2014 | Collier |
| 2014/0158588 A1 | 6/2014 | Pudil |
| 2014/0190876 A1 | 7/2014 | Meyer |
| 2014/0190885 A1 | 7/2014 | Meyer |
| 2014/0190886 A1 | 7/2014 | Pudil |
| 2014/0190891 A1 | 7/2014 | Lura |
| 2014/0216250 A1 | 8/2014 | Meyer |
| 2014/0217020 A1 | 8/2014 | Meyer |
| 2014/0217027 A1 | 8/2014 | Meyer |
| 2014/0217028 A1 | 8/2014 | Pudil |
| 2014/0217029 A1 | 8/2014 | Meyer |
| 2014/0217030 A1 | 8/2014 | Meyer |
| 2014/0220699 A1 | 8/2014 | Pudil |
| 2014/0224736 A1 | 8/2014 | Heide |
| 2014/0251908 A1 | 9/2014 | Ding |
| 2015/0057602 A1 | 2/2015 | Mason |
| 2015/0083647 A1 | 3/2015 | Meyer |
| 2015/0144539 A1 | 5/2015 | Pudil |
| 2015/0144542 A1 | 5/2015 | Pudil |
| 2015/0157960 A1 | 6/2015 | Pudil |
| 2015/0238673 A1 | 8/2015 | Gerber |
| 2015/0250937 A1 | 9/2015 | Pudil |
| 2015/0258268 A1 | 9/2015 | Collier |
| 2015/0352270 A1 | 12/2015 | Pudil |
| 2016/0038666 A1 | 2/2016 | Kelly |
| 2016/0166748 A1 | 6/2016 | Meyer |
| 2016/0166751 A1 | 6/2016 | Meyer |

(56) References Cited

U.S. PATENT DOCUMENTS

2016/0166752 A1    6/2016   Meyer
2016/0166753 A1    6/2016   Meyer

FOREIGN PATENT DOCUMENTS

| | | | |
|---|---|---|---|
| CN | 102307650 | | 1/2012 |
| CN | 202105667 | | 1/2012 |
| CN | 101237918 | | 1/2013 |
| CN | 101883584 | | 7/2013 |
| CN | 103209721 | * | 7/2013 ............ A61M 1/28 |
| CN | 103889481 | A1 | 6/2014 |
| CN | 103957960 | * | 7/2014 .......... A61M 1/1656 |
| CN | 201510761050.6 | | 8/2017 |
| DE | 3215003 | | 4/1985 |
| DE | 102011052188 | | 1/2013 |
| EP | 266795 | A2 | 11/1987 |
| EP | 0264695 | | 4/1988 |
| EP | 1124599 | | 5/2000 |
| EP | 1175238 | | 11/2000 |
| EP | 711182 | B1 | 6/2003 |
| EP | 2308526 | | 10/2003 |
| EP | 1364666 | A1 | 11/2003 |
| EP | 1523347 | | 1/2004 |
| EP | 1523350 | | 1/2004 |
| EP | 0906768 | B1 | 2/2004 |
| EP | 1691863 | | 4/2005 |
| EP | 2116269 | | 2/2008 |
| EP | 1450879 | | 10/2008 |
| EP | 1514562 | | 4/2009 |
| EP | 2219703 | | 5/2009 |
| EP | 1592494 | B1 | 6/2009 |
| EP | 1490129 | | 9/2009 |
| EP | 2100553 | A1 | 9/2009 |
| EP | 2398529 | | 11/2010 |
| EP | 2575827 | A2 | 12/2010 |
| EP | 2100553 | | 8/2011 |
| EP | 2388030 | | 11/2011 |
| EP | 2576453 | A2 | 12/2011 |
| EP | 2701580 | | 11/2012 |
| EP | 2701595 | | 11/2012 |
| EP | 1545652 | B1 | 1/2013 |
| EP | 1345856 | B1 | 3/2013 |
| EP | 2344220 | B1 | 4/2013 |
| EP | 1351756 | | 7/2013 |
| EP | 2190498 | | 7/2013 |
| EP | 1414543 | | 9/2013 |
| EP | 2701596 | | 3/2014 |
| EP | 2740502 | | 6/2014 |
| EP | 1787666 | | 11/2015 |
| FR | 2237639 | | 2/1977 |
| GB | 2479130 | | 5/2011 |
| JP | 60-132606 | | 7/1985 |
| JP | 60135064 | | 7/1985 |
| JP | 08504116 | | 5/1996 |
| JP | 2002306904 | | 10/2002 |
| JP | 2006325668 | A | 12/2006 |
| JP | 5099464 | | 10/2012 |
| JP | 2013521862 | | 6/2013 |
| WO | 9532010 | A1 | 11/1995 |
| WO | 1996040313 | | 12/1996 |
| WO | 9937342 | | 7/1999 |
| WO | 9937342 | A1 | 7/1999 |
| WO | WO2000057935 | A1 | 10/2000 |
| WO | 200066197 | A1 | 11/2000 |
| WO | 2000066197 | | 11/2000 |
| WO | 200170307 | A1 | 9/2001 |
| WO | 2001085295 | A2 | 9/2001 |
| WO | 0185295 | A2 | 11/2001 |
| WO | 2002043859 | | 6/2002 |
| WO | 2003043677 | A2 | 5/2003 |
| WO | 2003043680 | | 5/2003 |
| WO | 2003051422 | A2 | 6/2003 |
| WO | 2004008826 | | 1/2004 |
| WO | 2004009156 | | 1/2004 |
| WO | 2004030716 | A2 | 4/2004 |
| WO | 2004030717 | A2 | 4/2004 |
| WO | 2004064616 | A2 | 8/2004 |
| WO | 2004062710 | A3 | 10/2004 |
| WO | 2004105589 | A2 | 12/2004 |
| WO | 2005044339 | | 5/2005 |
| WO | 2004105589 | A3 | 6/2005 |
| WO | 2005061026 | | 7/2005 |
| WO | 2005123230 | | 12/2005 |
| WO | 2005123230 | A2 | 12/2005 |
| WO | 2006023589 | | 3/2006 |
| WO | 2006124431 | A2 | 11/2006 |
| WO | 2007010164 | A2 | 1/2007 |
| WO | 2007089855 | A2 | 8/2007 |
| WO | 2007146162 | A2 | 12/2007 |
| WO | 2007146162 | A3 | 12/2007 |
| WO | 2008037410 | | 4/2008 |
| WO | 2008051994 | | 5/2008 |
| WO | 2009026603 | | 12/2008 |
| WO | 2009024566 | | 2/2009 |
| WO | 2009026603 | A1 | 3/2009 |
| WO | 2009061608 | | 5/2009 |
| WO | 2009064984 | | 5/2009 |
| WO | 2009067071 | A1 | 5/2009 |
| WO | 2009071103 | | 6/2009 |
| WO | 2009094184 | | 7/2009 |
| WO | 2009132839 | A1 | 11/2009 |
| WO | 2009157877 | A1 | 12/2009 |
| WO | 2009157878 | A1 | 12/2009 |
| WO | 20090157877 | | 12/2009 |
| WO | 2010028860 | | 3/2010 |
| WO | 2010028860 | A1 | 3/2010 |
| WO | 2010042666 | | 4/2010 |
| WO | 2010042666 | A2 | 4/2010 |
| WO | 2010052705 | A1 | 5/2010 |
| WO | 2010062698 | | 6/2010 |
| WO | 2010096659 | | 10/2010 |
| WO | 2010121820 | | 10/2010 |
| WO | 2010102190 | A4 | 11/2010 |
| WO | 2011017215 | A1 | 2/2011 |
| WO | 2011025705 | A1 | 3/2011 |
| WO | 2011072337 | | 8/2011 |
| WO | 2011113572 | A1 | 9/2011 |
| WO | 2012026978 | | 3/2012 |
| WO | 2012042323 | | 4/2012 |
| WO | 2012050781 | | 4/2012 |
| WO | 2012051996 | | 4/2012 |
| WO | 2012067585 | | 5/2012 |
| WO | 2010042666 | A3 | 6/2012 |
| WO | 2012138604 | A2 | 10/2012 |
| WO | 2012148781 | | 11/2012 |
| WO | 2012148786 | | 11/2012 |
| WO | 2012148789 | | 11/2012 |
| WO | 2012162515 | A2 | 11/2012 |
| WO | 20120277551 | | 11/2012 |
| WO | 2012172398 | | 12/2012 |
| WO | 2013019179 | A1 | 2/2013 |
| WO | 2013019994 | A2 | 2/2013 |
| WO | 2013025844 | | 2/2013 |
| WO | 2013025844 | A2 | 2/2013 |
| WO | 2013027214 | | 2/2013 |
| WO | 2013028809 | A2 | 2/2013 |
| WO | 2013028809 | A3 | 2/2013 |
| WO | 2013019994 | A3 | 4/2013 |
| WO | 2013025844 | A3 | 5/2013 |
| WO | 2013103607 | A1 | 7/2013 |
| WO | 2013103906 | | 7/2013 |
| WO | 2013110906 | | 8/2013 |
| WO | 2013110919 | | 8/2013 |
| WO | 2013114063 | A1 | 8/2013 |
| WO | 2013121162 | A1 | 8/2013 |
| WO | 2013140346 | | 9/2013 |
| WO | 2013141896 | | 9/2013 |
| WO | 2013188861 | A1 | 12/2013 |
| WO | 14066254 | | 5/2014 |
| WO | 14066255 | | 5/2014 |
| WO | 14077082 | | 5/2014 |
| WO | 2014117000 | | 7/2014 |
| WO | 2014121158 | A1 | 8/2014 |
| WO | 2014121162 | | 8/2014 |

(56) References Cited

FOREIGN PATENT DOCUMENTS

| WO | 2014121163 | 8/2014 |
|---|---|---|
| WO | 2014121167 | 8/2014 |
| WO | 2014121169 | 8/2014 |
| WO | 2015071247 A1 | 5/2015 |

OTHER PUBLICATIONS

Examination report for Australian Application No. AU2014212135 dated May 25, 2017.
Office Action for Chinese Application 20148007136.3, dated Jun. 15, 2017.
PCT/US2012/034331, International Search Report and Written Opinion dated Jul. 9, 2012.
European Office Action in Application 14746793.0 dated Apr. 13, 2017.
European Search Report and Search Opinion for European Application EP15193720 dated May 2, 2016.
Office Action in European Application No. 15193720.8 dated Apr. 25, 2017.
Written Opinion for PCT/US2015/060090 dated Feb. 16, 2016.
International Preliminary Report on Patentability for PCT2015/060090 dated Jun. 13, 2017.
European Search Report for European Application EP 15193830.5 dated May 4, 2016.
Office Action for European Application No. 15193645.7 dated Apr. 21, 2017.
2017-530641_OA .
Office Action in U.S. Appl. No. 13/757,709 dated Jan. 7, 2016.
Office Action in U.S. Appl. No. 13/757,693 dated Nov. 13, 2015.
Office Action in U.S. Appl. No. 13/757,693 dated May 23, 2016.
Office Action in U.S. Appl. No. 13/757,709 dated Jun. 6, 2015.
U.S. Appl. No. 61/480,544.
Office Action in U.S. Appl. No. 13/757,794 dated Oct. 21, 2015.
Office Action in U.S. Appl. No. 13/757,794 dated May 2, 2016.
Office Action in U.S. Appl. No. 13/424,525 dated Aug. 11, 2015.
Office Action in U.S. Appl. No. 13/424,525 dated Feb. 25, 2016.
Office Action in U.S. Appl. No. 13/424,525 dated Jun. 17, 2016.
Office Action in U.S. Appl. No. 13/424,525 dated Oct. 20, 2016.
Office Action in U.S. Appl. No. 13/424,479 dated Nov. 24, 2014.
Office Action in U.S. Appl. No. 14/566,686 dated Apr. 28, 2016.
Office Action in U.S. Appl. No. 13/424,533 dated Oct. 22, 2013.
Office Action in U.S. Appl. No. 13/424,533 dated Apr. 18, 2014.
Office Action in U.S. Appl. No. 13/424,533 dated Jan. 5, 2015.
Office Action in U.S. Appl. No. 13/424,533 dated Jun. 2, 2015.
Office Action in U.S. Appl. No. 13/424,533 dated Jul. 14, 2016.
Welgemoed, T.J., Capacitive Deionization Technology: An Alternative to desalination Solution, Desalination 183 (2005) 327-340.
European Search Report for App. No. 15193645.7, dated Apr. 15, 2016.
European Search Report in App. No. 15193720.8 dated Apr. 26, 2016.
EP. App. 14746193.3 Search Report dated Oct. 19, 2016.
Office Action in U.S. Appl. No. 14/555,393 dated May 4, 2016.
Office Action in U.S. Appl. No. 14/555,393 dated Nov. 1, 2016.
Office Action in U.S. Appl. No. 14/555,414 dated May 4, 2016.
Office Action in U.S. Appl. No. 14/555,414 dated Nov. 3, 2016.
Office Action in U.S. Appl. No. 13/586,824 dated Dec. 21, 2015.
Office Action in U.S. Appl. No. 13/586,824 dated Jun. 4, 2016.
Office Action in Chinese Application No. 201480007138.2 dated Sep. 28, 2016.
Ruperez et al., Comparison of a tubular pulsatile pump and a volumetric pump for continuous venovenous renal replacement therapy in a pediatric animal model, 51 ASAIO J. 372, 372-375 (2005).
St. Peter et al., Liver and kidney preservation by perfusion, 359 The Lancet 604, 606(2002).
Dasselaar et al., Measurement of relative blood volume changes during hemodialysis: merits and limitations, 20 Nephrol Dial Transpl. 2043, 2043-2044 (2005).
Ralph T. Yang, Adsorbents: Fundamentals and Applications 109 (2003).
Henny H. Billett, Hemoglobin and Hematocrit, in Clinical Methods: The History, Physical, and Laboratory Examinations 719(HK Walker, WD Hall, & JW Hurst ed., 1990).
Office Action in U.S. Appl. No. 13/565,733 dated Jan. 11, 2016.
Office Action in U.S. Appl. No. 13/565,733 dated Jun. 11, 2015.
Office Action in U.S. Appl. No. 13/586,824 dated Jun. 4, 2015.
Office Action in U.S. Appl. No. 13/757,792 dated Jun. 2, 2016.
Office Action in U.S. Appl. No. 13/757,796 dated Apr. 13, 2015.
Office Action in U.S. Appl. No. 13/757,796 dated Dec. 21, 2015.
Office Action in U.S. Appl. No. 13/835,735 dated Oct. 13, 2015.
Office Action in U.S. Appl. No. 13/836,079 dated Apr. 17, 2015.
Office Action in U.S. Appl. No. 13/836,079 dated Jun. 30, 2016.
Office Action in U.S. Appl. No. 13/791,755 dated Mar. 16, 2016.
Office Action in U.S. Appl. No. 13/791,755 dated Aug. 9, 2016.
Office Action in U.S. Appl. No. 13/835,735 dated Jun. 16, 2016.
Office Action in U.S. Appl. No. 13/836,079 dated Nov. 6, 2015.
Office Action in U.S. Appl. No. 13/791,755 dated Sep. 10, 2015.
Office Action in U.S. Appl. No. 13/791,755 dated Apr. 20, 2015.
U.S. Appl. No. 13/424,467.
Office Action in U.S. Appl. No. 14/259,589 dated Nov. 4, 2016.
Office Action in U.S. Appl. No. 14/261,651 dated Aug. 25, 2016.
International Search Report from International Application No. PCT/US2014/014347 dated May 9, 2014.
International Search Report for PCT/US2015/060090 date of completion is Feb. 9, 2016 (3 pages).
St. Peter et al., Liver and Kidney Preservation by perfusion, 369 The Lancet 604, 606 (2002).
Office Action for Chinese Application 20148007136.3, dated Jun. 2, 2016.
Office Action for Chinese Application 20148007136.3, dated Jan. 26, 2017.
Franks, Gene, Cabon Filtration: What it does, What it doesnt, Mar. 14, 2012, pp. 1-3.
Franks, Gene, Carbon Filtration: What it does, What it doesnt, Mar. 14, 2012, pp. 1-3.
PCT/US2014/014352 International Search Report and Written Opinion Jul. 7, 2014.
PCT/US2014/014352 International Prelminary Report on Patentability, Aug. 14, 2015.
Hamm et al,. Sorbent regenerative hemodialysis as a potential cuase of acute hypercapnia, Kidney International, vol. 21, (1982), pp. 416-418.
Office Action in Chinese Application No. 201480007132.5 dated Jul. 19, 2017.
EP Search Report for Application No. 16204175.0 dated Mar. 29, 2017.
Office Action for Chinese Application 201510713880.1 dated Apr. 1, 2017.
U.S. Appl. No. 13/424,533.
Understanding Dialysate Bicarbonate—A simple approach to understanding a complex equation by Fresenius Medical Care, 2011.
International Search Report, Application PCT/US2016/043948, dated Feb. 2, 2017.
Written Opinion, Application PCT/2016/043948, dated Feb. 2, 2017.
International Search Report, Application PCT/US2016/043935, dated Feb. 2, 2017.
Written Opinion, Application PCT/US2016/043935, dated Feb. 2, 2017.
International Search Report and Written Opinion in App. No. PCT/US2012/049398 dated Feb. 25, 2013.
Office Action in European App. No. 12819714.2 dated Aug. 5, 2016.
PCT/US2014/014343 Written Opinion dated Jan. 2, 2015.
PCT/US2014/014343 International Preliminary Search Report dated Mar. 18, 2015.
European Search Report for EP Appl. No. 1474679.4 dated Aug. 19, 2016.

(56) References Cited

OTHER PUBLICATIONS

Office Action for Chinese Application 201510761050.6 dated Aug. 2, 2017.
PCT/US2014/014355 International Search Report and Written Opinion dated May 1, 2014.
PCT/US2014/014355 International Preliminary Report dated Apr. 13, 2015.
EP 14746817.7 European Search Report dated Sep. 27, 2016.
Office Action in Chinese Application No. 201480007132.5 dated Feb. 27, 2017.
Office Action in Chinese Application No. 201280047921.2 dated Jun. 11, 2015.
International Preliminary Report from International Application No. PCT/US2014/014348 dated Jan. 9, 2015.
European Search Report from European Application No. EP 14746193.3 dated Oct. 19, 2016.
European Search Report from European Application No. EP 14746193.3 dated Jun. 8, 2016.
PCT/US2014/014346 Writtent Opinion dated Apr. 10, 2015.
PCT/US2014/014346 International Search Report and Writtent Opinion dated May 23, 2014.
EP 14746415.0 European Search Report dated Aug. 22, 2016.
Office Action in European Application No. EP 14746415.0 dated Apr. 19, 2017.
PCT/US2014/014357 International Search Report and Written Opinion dated May 19, 2014.
PCT/US2014/014357 Written Opinion dated Feb. 18, 2015.
European Search Report in European Application No. EP 14746010.9 dated Sep. 15, 2016.
Office Action in European Application No. 14746415.0 dated Apr. 19, 2017.
U.S. Appl. No. 13/424,490.
U.S. Appl. No. 13/424,517.
EP 13733819 Supplementary European Search Report dated Jan. 28, 2015.
EP Search Report and Opinion for Application No. 15193720.8 dated May 2, 2016.
Office action for European Application No. 15193720.8 dated Apr. 25, 2017.
PCT/US2012/051011, International Search Report and Written Opinion, Mar. 4, 2013.
Brynda, et. al., The detection of toman 2-microglcbuiin by grating coupler immunosensor with three dimensional antibody networks. Biosensors & Bioelectronics, 1999, 363-368, 14(4).
Zhong, et. al., Miniature urea sensor based on H(+)-ion sensitive field effect transistor and its application in clinical analysis, Chin. J. Biotechnol., 1992, 57-65. 8(1).
Roberts M, The regenerative dialysis (REDY) sorbent system. Nephrology, 1998, 275-278:4.
U.S. Appl. No. 61/480,541, filed Apr. 29, 2011.
Hemametrics, Crit-Line Hematocrit Accuracy, 2003, 1-5, vol. 1, Tech Note No. 11 (Rev. D).
Weissman, S., et al., Hydroxyurea-induced hepatitis in human immunodeficiency virus-positive patients. Clin. Infec. Dis, (Jul. 29, 1999): 223-224.
PCT/US2012/034334, International Search Report, dated Jul. 6, 2012.
PCT/US2012/034335, International Search Report, dated Sep. 5, 2012.
PCT/US/2012/034327, International Search Report, dated Aug. 13, 2013.
PCT/US/2012/034329, International Search Report, dated Dec. 3, 2012.
EP13182115.9-1651 European Search Report, dated Feb. 3, 2014.
International Search Report from PCT/US2012/051946 dated Mar. 4, 2013.
U.S. Appl. No. 61/526,209.
Written Opinion of the International Searching Authority for PCT/US2012/049398 dated Feb. 25, 2013.
Wang, Fundamentals of intrathoracic impedance monitoring in heart failure, Am. J. Cardiology, 2007, 3G-10G: Suppl.
PCT/US2014/067650 International Search Report Written Opinion dated Mar. 9, 2015.
Bleyer, et al, Kidney International. Jun. 2006; 69(12):2268-2273.
U.S. Appl. No. 29/446,285, filed Feb. 1, 2013.
Marchant, et. al., In vivo Biocompatibility Studies 1: The Cage Implant System and a Biodegradable Hydrogel, J. Biomed. Mat. Res., 1983, 301-325: 17.
Bleyer, et. al., Sudden and cardiac death rated in hemodialysis patients, Kidney International. 1999, 1553-1559: 55.
PCT/US2012/025711, International Search Report dated Jul. 4, 2012.
PCT/US2013/020404, International Search Report, dated Jan. 4, 2013.
PCT/US2012/034333, International Preliminary Report on Patentability, dated Oct. 29, 2013.
PCT/US2012/034333, International Search Report, dated Aug. 29, 2012.
PCT/US2012/034333, International Search Report, dated Aug. 29, 2013.
PCT/US2012/051011, International Search Report, dated Jan. 17, 2014.
PCT/US2012/034330, International Preliminary Report on Patentability, dated Oct. 29, 2013.
Culleton, BF et al. Effect of Frequent Nocturnal Hemodialysis vs. Conventional Hemodialysis on Left Ventricular Mass and Quality of Life. 2007 Journal of the American Medical Association 298 (11), 1291-1299.
U.S. Appl. No. 13/757,722, filed Feb. 1, 2013.
U.S. Appl. No. 13/757,794, filed Feb. 2, 2012.
U.S. Appl. No. 13/791,755, filed Mar. 8, 2013.
U.S. Appl. No. 13/424,479, filed Nov. 1, 2012.
U.S. Appl. No. 13/757,792, filed Feb. 2, 2013.
U.S. Appl. No. 13/757,794, filed Feb. 2, 2013.
U.S. Appl. No. 13/837,287, filed Mar. 15, 2013.
U.S. Appl. No. 13/424,429 dated Nov. 1, 2012.
Redfield, et. al, Restoration of renal response to atria! natriuretic factor in experimental low-output heat failure, Am. J. Physiol., Oct. 1, 1989, R917-923:257.
Rogoza, et. al., Validation of A&D UA-767 device for the self-measurement of blood pressure, Blood Pressure Monitoring, 2000, 227-231, 5(4).
Lima, et. al., An electrochemical sensor based on nanostructure hollsndite-type manganese oxide for detection of potassium ion, Sensors, Aug. 24, 2009, 6613-8625, 9.
MacLean, et, al., Effects of hindlimb contraction on pressor and muscle interstitial metabolite responses in the cat, J. App. Physiol., 1998, 1583-1592, 85(4).
U.S. Appl. No. 13/757,693, filed Feb. 1, 2013.
PCT Application, PCT/US20013/020404, filed Jan. 4, 2013.
U.S. Appl. No. 13/424,525.
U.S. Appl. No. 13/836,973, filed Mar. 15, 2013.
U.S. Appl. No. 14/259,655, filed Apr. 23, 2014.
U.S. Appl. No. 14/259,589, filed Apr. 23, 2014.
U.S. Appl. No. 13/757,693, filed Jan. 4, 2013.
U.S. Appl. No. 13/836,079, filed Mar. 15, 2013.
U.S. Appl. No. 14/240,129, filed Aug. 22, 2013.
PCT/US2014/014346 International Search Report and Written Opinion.
U.S. Appl. No. 13/835,735, filed Mar. 15, 2013.
PCT/US2014/014345 International Search Report and Written Opinion, dated May 2014.
U.S. Appl. No. 13/835,735 IDS, filed Jun. 13, 2013.
Ronco et al. 2008, Cardiorenal Syndrome, Journal American College Cardiology, 52:1527-1539, Abstract.
Overgaard, et. al., Activity-induced recovery of excitability in K+-depressed rat soleus muscle, Am. J. p. 280: R48-R55, Jan 1, 2001.
Overgaard. et. al., Relations between excitability and contractility in rate soleusmuscle: role of the Na+—K+ pump and Na+—K—S gradients. Journal of Physiology, 1999, 215-225, 518(1).

(56) References Cited

OTHER PUBLICATIONS

Coast, et al. 1990, An approach to Cardiac Arrhythmia analysis Using Hidden Markov Models, IEEE Transactions On Biomedical Engineering. 1990, 37(9):826-835.
Weiner, et. al., Article: Cardiac Function and Cardiovascular Disease in Chronic Kidney Disease, Book: Primer on Kidney Diseases (Author: Greenberg, et al), 2009,499-505, 5th Ed., Saunders Elsevier, Philadelphia, PA.
U.S. Appl. No. 61/480,532.
U.S. Appl. No. 13/424,479.
U.S. Appl. No. 13/424,429, filed Nov. 1, 2012.
U.S. Appl. No. 61/480,530.
U.S. Appl. No. 61/480,528, filed Apr. 29, 2011.
Secemsky, et. al, High prevalence of cardiac autonomic dysfunction and T-wave alternans in dialysis patients. Heart Rhythm, Apr. 2011, 592-598 : vol. 8, No. 4.
Wei, et. al., Fullerene-cryptand coated piezoelectric crystal urea sensor based on urease, Analytica Chimica Acta, 2001,77-85:437.
Gambro AK 96 Dialysis Machine Operators Manual, Dec. 2012. p. 1-140.
Gambro AK 96 Dialysis Machine Operators Manual, Dec. 2012. p. 141-280.
Gambro AK 96 Dialysis Machine Operators Manual, Dec. 2012. p. 281-420.
Gambro AK 96 Dialysis Machine Operators Manual, Dec. 2012. p. 421-534.
European Search Report 12819714.2-1651/2739325 PCT/US2012049398, dated Jun. 12, 2015.
PCT/US2014/14343 Intl Search Report & Written Opinion, dated May 9, 2014.
PCT/US2014/014350 International Search Report and Written Opinion dated May 2014.
U.S. Appl. No. 13/368,225, filed Feb. 7, 2012.
EP 14746793 Supplementary European Search Report dated Aug. 18, 2016.
EP 14746791 Supplementary European Search Report dated Aug. 19, 2016.
EP 14746799 Supplementary European Seach Report dated Aug. 18, 2016.
Leifer et al., A Study on the Temperature Variation of Rise Velocity for Large Clean Bubbles, J. Atmospheric & Oceanic Tech., vol. 17, pp. 1392-1402, Oct. 2000.
Talaia, Terminal Velocity of a Bubble Rise in a Liquid Column, World Acad. of Sci., Engineering & Tech., vol. 28, pp. 264-268, Published Jan. 1, 2007.
The FHN Trial Group. In-Center. Hemodialysis Six Times per Week versus Three Times per Week, New England Journal of Medicine, 2010 Abstract.
PCT/US2012/034332, International Search Report, dated Jul. 5, 2012.
Office Action in U.S. Appl. No. 13/757,717 dated Dec. 26, 2014.
Office Action in U.S. Appl. No. 13/757,728 dated Jan. 8, 2016.
Office Action in U.S. Appl. No. 13/757,728 dated Aug. 12, 2016.
Office Action in U.S. Appl. No. 13/836,538 dated Aug. 19, 2015.
Siegenthaler, et al., Pulmonary fluid status monitoring with intrathoracic impedance, Journal of Clinical Monitoring and Computing, 24:449-451, published Jan. 12, 2011.
Office Action in U.S. Appl. No. 13/836,538 dated Jan. 11, 2016.
Office Action in U.S. Appl. No. 13/836,538 dated Apr. 27, 2016.
Office Action in U.S. Appl. No. 13/757,722 dated May 19, 2016.
Office Action for European Application No. 14746611.4 dated Jan. 3, 2017.
Supplemental Search Report and Search Opinion for European Application No. 14746611.4 dated Aug. 18, 2016.
Office Action in Chinese Application No. 201480007138.2 dated May 31, 2017.
Office Action in European Application No. 14746193.3 dated Apr. 19, 2017.
Examination report in Australian Application No. 2014212141 dated May 26, 2017.
Examination report for Australian Application 2015361083 dated Jul. 20, 2017.
U.S. Appl. No. 61/480,539 dated Apr. 29, 2011.
U.S. Appl. No. 61/480,535 dated Apr. 29, 2011.
Nedelkov, et. al., Design of buffer exchange surfaces and sensor chips for biosensor chip mass spectrometry, Proteomics, 2002, 441-446, 2(4).
PCT/US2017/025868 International Search Report dated Jun. 29, 2017.
PCT/US2017/025868 Written Opinion dated Jun. 29, 2017.
PCTUS2017025858 International Search Report dated Jun. 29, 2017.
PCTUS2017025858 Written Opinion dated Jun. 29, 2017.
PCTUS2017025876 International Search Report dated Jun. 29, 2017.
PCTUS2017025876 Written Opinion dated Jun. 29, 2017.

* cited by examiner

DEGASSING SYSTEM FOR DIALYSIS

CROSS-REFERENCE TO RELATED APPLICATIONS

This application is a continuation of U.S. patent application Ser. No. 14/566,686 filed Dec. 10, 2014, and the disclosure of the above-identified application is hereby incorporated by reference in its entirety.

FIELD OF THE INVENTION

The invention relates to a degassing vessel and related systems and methods that can remove certain gases such as carbon dioxide from a dialysis system. The invention further relates to mechanical systems and methods for degassing a dialysate or any fluid used for, during or resulting from dialysis.

BACKGROUND

In dialysis systems including sorbent based systems, certain amounts of gas such as carbon dioxide can be created by the breakdown of urea into ammonia and carbon dioxide by urease. The resulting gas can go into solution in a fluid such as a dialysate and/or form gas bubbles. The bicarbonate buffer system can also contribute to the creation of excess carbon dioxide in dialysis fluid. Removal of carbon dioxide and other dissolved and undissolved gases in a dialysis system can be important in order to maintain a required pH, certain fluid conditions such as bicarbonate or ion concentration, and avoid the creation of gas bubbles. For example, a desired partial pressure of carbon dioxide may be required for safe operation of dialysis. Additionally, gas bubbles can interfere with the smooth pumping of the dialysate in the dialysate loop, interfere with sensors in the dialysate flow loop, reduce diffusive clearance across the dialysis membrane, and can present a dangerous condition for a patient if the gas crosses the dialyzer membrane into the extracorporeal circuit and causes gas bubbles in the blood returning to the patient.

However, the water used to initially prepare a dialysate may contain a significant amount of dissolved gases, such as nitrogen and oxygen. Further, carbon dioxide may be formed as part of the breakdown of urea as spent dialysate flows through the sorbent cartridge. Dissolved gases may come out of solution in the dialysate flow loop, creating bubbles and interfering with sensors and the ability of the pumps of the dialysis system to smoothly pump fluid. In addition to carbon dioxide from the breakdown of urea, dialysate can also contain dissolved oxygen and nitrogen gas that crosses the dialysis membrane from the patient's blood.

The degassers known in the art do not necessarily efficiently remove dissolved gases, such as carbon dioxide, from fluid, or do not provide control over the amount of carbon dioxide removed. Hence, there is a need for a degasser that can remove large amounts of dissolved carbon dioxide from solution, while providing control over the amount of dissolved and undissolved gases removed from fluid before, during and after dialysis therapy. There is also a need for a degasser having the small size and weight necessary for a portable device.

SUMMARY OF THE INVENTION

The first aspect of the invention is drawn to a degassing vessel. In any embodiment of the first aspect of the invention, the degassing vessel can comprise a fluid inlet in the degassing vessel fluidly connected to a flow restriction; a fluid outlet in the degassing vessel for fluid connection to a fluid pump downstream of the degassing vessel; and a gas outlet for fluid connection to a vacuum pump.

In any embodiment of the first aspect of the invention, the degassing vessel can further comprise a carbon dioxide sensor positioned to detect carbon dioxide at the outlet of the degassing vessel.

In any embodiment of the first aspect of the invention, the degassing vessel can further comprise one or more selected from the group consisting of a degas sprayer, a nucleation chamber, and combinations thereof; wherein fluid entering the degassing vessel through the fluid inlet passes through any of the degas sprayer, the nucleation chamber, or the combinations thereof.

In any embodiment of the first aspect of the invention, the flow restriction can be comprised of a degas sprayer, a nucleation chamber, or both the degas sprayer and the nucleation chamber.

In any embodiment of the first aspect of the invention, the flow restriction can be selected from the group consisting of orifices, venturis, spray nozzles, a narrowing, pinch valves, gate valves, variable orifice valves, a pressure regulator, and combinations thereof.

In any embodiment of the first aspect of the invention, the degassing vessel can comprise a pressure sensor configured to determine a fluid pressure in the degassing vessel.

In any embodiment of the first aspect of the invention, the degassing vessel can further comprise one or more sensors in the degassing vessel; the one or more sensors are configured to determine the fluid level in the degassing vessel.

In any embodiment of the first aspect of the invention, the one or more sensors can comprise an upper level sensor and a lower level sensor in the degassing vessel; wherein the upper level sensor detects whether the fluid level in the degassing vessel is above a first pre-set point; and wherein the lower level sensor detects whether the fluid level in the degassing vessel is below a second pre-set point.

In any embodiment of the first aspect of the invention, the degassing vessel can further comprise an overflow float in the degassing vessel, the overflow float being of a lower density than water; and a mechanical vent valve placed on the degassing vessel at the gas outlet, such that if the fluid level in the degassing vessel is above a pre-set point, the overflow float will cover the mechanical vent valve or the float can move an actuator that leads to blocking fluid from passing through the mechanical vent valve.

Any of the features disclosed as being part of the first aspect of the invention can be included in the first aspect of the invention, either alone or in combination.

The second aspect of the invention is drawn to a degassing system. In any embodiment of the second aspect of the invention, the degassing system can have a degassing vessel having a fluid inlet, and a fluid outlet, a degas flow restrictor fluidly connected to the inlet of the degassing vessel, a fluid pump fluidly connected to the degassing vessel, and located downstream of the degassing vessel, for pulling fluid into the degassing vessel through the fluid inlet and out of the degassing vessel through the fluid outlet; and a vacuum pump attached to the degassing vessel for removing gas from the degassing vessel.

In any embodiment of the second aspect of the invention, the degassing system can further comprise one or more of a degas sprayer located inside the degassing vessel at the fluid inlet of the degassing vessel such that fluid entering the degassing vessel through the fluid inlet passes through the degas sprayer, a nucleation chamber located either between the degas flow restrictor and the degassing vessel or inside the degassing vessel, and combinations thereof.

In any embodiment of the second aspect of the invention, the degassing system can further comprise a nucleation chamber, wherein the nucleation chamber is located between the degas flow restrictor and the degassing vessel or the nucleation chamber is located inside the degassing vessel.

In any embodiment of the second aspect of the invention, the selected nucleation chamber can comprise one or more of glass beads, fiber mesh and a filter.

In any embodiment of the second aspect of the invention, the degassing system can further comprise a carbon dioxide sensor located downstream of the degassing vessel.

In any embodiment of the second aspect of the invention, the degassing system can further comprise a control unit in electronic communication with the carbon dioxide sensor, the vacuum pump and the fluid pump.

In any embodiment of the second aspect of the invention, the control unit can automatically adjust the pump rates of the fluid pump and the vacuum pump in response to the information received from the carbon dioxide sensor.

In any embodiment of the second aspect of the invention, the degassing system can further comprise a vent valve positioned on a connector, wherein the connector is attached to the degassing vessel, and wherein gas can flow out of the degassing vessel through the vent valve.

In any embodiment of the second aspect of the invention, the degassing system can be positioned in a degassing flow loop wherein the degassing flow loop is fluidly connected to a dialysate flow loop and is parallel to the dialysate flow loop; and wherein the flow rate of the fluid in the degassing flow loop can be operated independently of the flow rate of the fluid in the dialysate flow loop.

In any embodiment of the second aspect of the invention, the degassing flow loop can be parallel to the dialysate flow loop.

In any embodiment of the second aspect of the invention, air can be drawn into the degassing vessel through the vent valve and out through a fluid port of the degassing vessel.

In any embodiment of the second aspect of the invention, the degassing system can comprise a particle filter in fluid communication with the vent valve such that air that is forced into the system through the vent valve first passes through the particle filter.

In any embodiment of the second aspect of the invention, the degassing system can comprise a pressure sensor located between the degas flow restrictor and the fluid pump. In any embodiment of the second aspect of the invention, the pressure sensor can be used to measure the operating pressure in the degassing system.

In any embodiment of the second aspect of the invention, the vacuum pump can pump gas removed from the degassing vessel to a fluid drain line of the dialysate flow path.

In any embodiment of the second aspect of the invention, the vent port can be in fluid communication through a control valve to the dialysate flow path.

In any embodiment of the second aspect of the invention, the flow restrictor can comprise a pressure regulator. In any embodiment of the second aspect of the invention, the flow restrictor can cause the restriction to vary such that a predetermined pressure is maintained in the degasser.

In any embodiment of the second aspect of the invention, the fluid pump and vacuum pump can be any one of a gear pump, a peristaltic pump, a diaphragm pump or an impeller pump, or combinations thereof.

In any embodiment of the second aspect of the invention, the degassing system can comprise a sensor positioned on the fluid pump to monitor the wear of the fluid pump.

In any embodiment of the second aspect of the invention, the degassing system can comprise one or more sensors in the degassing vessel; wherein the one or more sensors detect or measure the fluid level in the degassing vessel; wherein if the one or more sensors detect that the fluid level in the degassing vessel is above a first pre-set point, either the pump rate of the fluid pump is increased, the pump rate of the vacuum pump is decreased, or a combination thereof; and if the one or more sensors detect that the fluid level in the degassing vessel is below a second pre-set point, either the pump rate of the fluid pump is decreased, the pump rate of the vacuum pump is increased, or a combination thereof.

In any embodiment of the second aspect of the invention, the fluid pump and vacuum pump can be capable of creating an absolute pressure in the degassing vessel of between any of 60 mmHg and 200 mmHg, 60 mmHg and 100 mmHg, 80 mmHg and 150 mmHg, and 100 mmHg and 200 mmHg. In any embodiment of the second aspect of the invention, the fluid pump and vacuum pump can be capable of creating an absolute pressure in the degassing vessel of between any of 60 mmHg and 200 mmHg, 60 mmHg and 100 mmHg, 80 mmHg and 150 mmHg, and 100 mmHg and 200 mmHg.

In any embodiment of the second aspect of the invention, if the one or more sensors detect that the fluid level in the degassing vessel is above a first pre-set point, either the pump rate of the fluid pump can be automatically increased, the pump rate of vacuum pump can be automatically reduced, or a combinations thereof, and if the one or more sensors detect that the fluid level in the degassing vessel is below a second pre-set point, either the pump rate of the fluid pump can be automatically decreased, the pump rate of vacuum pump can be automatically increased, or a combination thereof.

In any embodiment of the second aspect of the invention, the degassing system can comprise an overflow float in the degassing vessel, the overflow float being of a lower density than water.

In any embodiment of the second aspect of the invention, the degassing system can comprise a mechanical vent valve placed on the degassing vessel before the connector with the vent valve, such that if the fluid level in the degassing vessel is above a pre-set point, the overflow float will cover the mechanical vent valve or the float can move an actuator and that leads to blocking fluid from passing into the connector, while still allowing air to enter and exit the degassing vessel through the mechanical vent valve.

In any embodiment of the second aspect of the invention, the liquid pump can cause the flow through the degassing flow loop to be faster than the flow through the dialysate flow loop.

In any embodiment of the second aspect of the invention, the degassing system can be fluidly connected to a controlled compliant dialysis system.

In any embodiment of the second aspect of the invention, the degassing system can be part of the dialysate flow path of a recirculating regenerative sorbent-based hemodialysis system.

In any embodiment of the second aspect of the invention, the fluid pump and vacuum pump can be capable of creating a pressure differential of between any of −1500 and 700 mmHg, −1500 and 0 mmHg, 0 and 500 mmHg, 400 and 700 mmHg, 400 and 500 mmHg, 450 and 600 mmHg, or 550 and 700 mmHg.

In any embodiment of the second aspect of the invention, the degassing system can comprise a semi-permeable membrane between the vacuum pump and the degassing vessel, wherein the semi-permeable membrane allows gas to pass through the membrane but does not allow liquid to pass through the membrane.

In any embodiment of the second aspect of the invention, the degassing system can comprise a control unit in electronic communication with the pressure sensor and at least one of the fluid pump, vacuum pump or flow restrictor.

In any embodiment of the second aspect of the invention, the control unit can automatically adjust the pump rates of the fluid pump or the vacuum pump in response to the information received from the pressure sensor.

In any embodiment of the second aspect of the invention, the control unit can automatically adjust the amount of flow restriction caused by the flow restrictor.

In any embodiment of the second aspect of the invention, in response to a signal from the carbon dioxide sensor showing that the carbon dioxide concentration is above a pre-set point, the control unit can be configured to automatically do one or more of increase the pump rate of the fluid pump, increase the pump rate of the vacuum pump, or a combination thereof.

In any embodiment of the second aspect of the invention, in response to a signal from the carbon dioxide sensor showing that the carbon dioxide concentration is below a pre-set point, the control unit can be configured to automatically do one or more of: shut off the fluid pump, shut off the vacuum pump, decrease the pump rate of the fluid pump, decrease the pump rate of the vacuum pump, or a combination thereof.

In any embodiment of the second aspect of the invention, the degassing system can comprise a vent line, wherein the vent line is in fluid communication with a recirculating dialysate flow path.

In any embodiment of the second aspect of the invention, fluid can be recirculated through the vent line and vent valve to a recirculating dialysate flow path.

In any embodiment of the second aspect of the invention, the fluid recirculated through the vent line and vent valve can be a fluid for cleaning or disinfection.

Any of the features disclosed as being part of the second aspect of the invention can be included in the second aspect of the invention, either alone or in combination.

The third aspect of the invention is drawn to a method for controlling the amount of carbon dioxide in a fluid. In any embodiment of the third aspect of the invention, the method can include lowering the pressure of a fluid, inducing bubbles to come out of solution, and collecting the gas from the bubbles at a pressure below atmospheric pressure.

In any embodiment of the third aspect of the invention, the step of inducing bubbles to come out of solution can comprise passing the fluid through a sprayer. In any embodiment of the third aspect of the invention, the step of inducing bubbles to come out of solution can comprise passing the fluid through a nucleation chamber.

In any embodiment of the third aspect of the invention, the method can include directing the fluid into a degasser, wherein the degasser comprises a degassing vessel having a fluid inlet, and a fluid outlet; a degas flow restrictor disposed upstream of the degassing vessel; a liquid pump fluidly connected to the degassing vessel and located downstream of the degassing vessel, for pulling fluid into the degassing vessel through the fluid inlet and out of the degassing vessel through the fluid outlet; a vacuum pump attached to the degassing vessel for removing gas from the degassing vessel; and a carbon dioxide sensor located downstream of the degassing vessel; and adjusting the pump rates of the vacuum pump and the fluid pump in response to the data received from the carbon dioxide sensor.

In any embodiment of the third aspect of the invention, the degasser can further comprise a control unit in electronic communication with the carbon dioxide sensor, the fluid pump and the vacuum pump; and the control unit automatically makes the adjustments to the pump rates of the vacuum pump and the fluid pump in response to the data received from the carbon dioxide sensor.

In any embodiment of the third aspect of the invention, in response to a signal from the carbon dioxide sensor showing that the carbon dioxide level is above a pre-set point the method can comprise one or more of increasing the pump rate of the fluid pump or increasing the pump rate of the vacuum pump.

In any embodiment of the third aspect of the invention, in response to a signal from the carbon dioxide sensor showing that the carbon dioxide level is below a pre-set point the method can comprise one or more of: shut off the fluid pump, shut off the vacuum pump, and decrease the pump rate of the fluid pump, or decrease the pump rate of the vacuum pump.

In any embodiment of the third aspect of the invention, the rate of the fluid pump can be controlled in proportion to the rate of the dialysate pump.

In any embodiment of the third aspect of the invention, the rate of the fluid pump can be controlled at varying flow rates and a variable degas restrictor can coordinately change the amount of flow restriction in the degassing loop to maintain a predetermined pressure in the degasser.

In any embodiment of the third aspect of the invention, the rate of the vacuum pump can be increased to raise the level of liquid in the degassing vessel or decreased to reduce the level of fluid in the degassing vessel.

In any embodiment of the third aspect of the invention, a sensor can be used to measure the level of liquid in the degassing vessel and the controller can adjust the rate of the vacuum pump the achieve the desired liquid level in the degassing vessel.

Any of the features disclosed as being part of the third aspect of the invention can be included in the third aspect of the invention, either alone or in combination.

DETAILED DESCRIPTION OF THE INVENTION

Figure 1A:
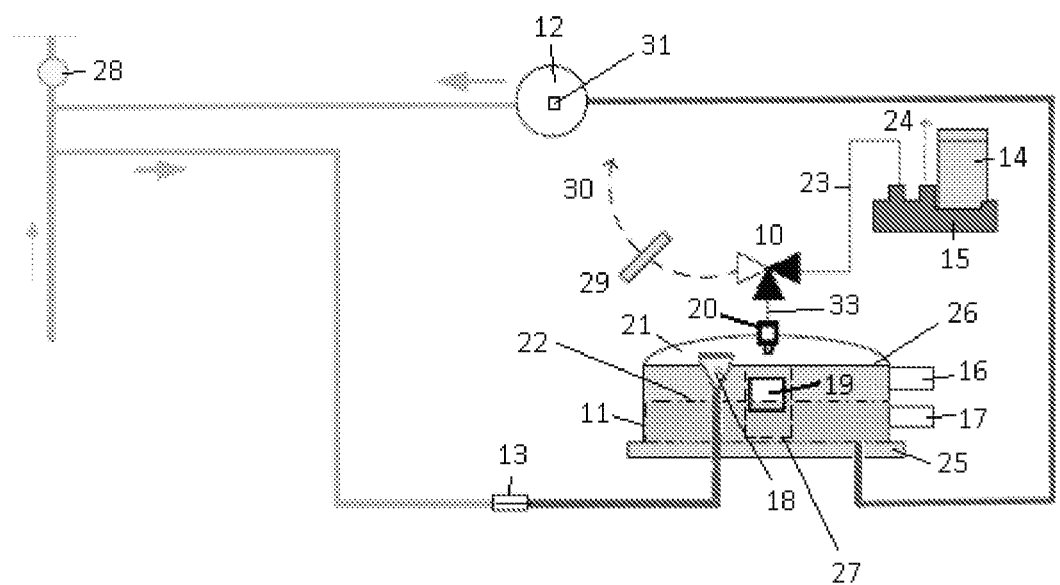
FIG. 1a shows a schematic of a degassing module for use in sorbent dialysis configured to degas dialysate.

Unless defined otherwise, all technical and scientific terms used herein generally have the same meaning as commonly understood by one of ordinary skill in the relevant art.

The articles "a" and "an" are used herein to refer to one or to more than one (i.e., to at least one) of the grammatical object of the article. By way of example, "an element" means one element or more than one element.

The term "cartridge" refers to any container designed to contain a powder, fluid, or gas made for ready connection to a device or mechanism. The container can have one or more compartments. Instead of compartments, the container can also be comprised of a system of two or more modules connected together to form the cartridge wherein the two or more modules once formed can be connected to a device or mechanism.

The term "carbon dioxide sensor" refers to devices that can detect or measure the concentration of carbon dioxide in a liquid or gas.

The terms "communicate" and "communication" include, but are not limited to, the connection of system electrical elements, either directly or remotely, for data transmission among and between said elements. The terms also include, but are not limited to, the connection of system fluid elements enabling fluid interface among and between said elements.

The term "comprising" includes, but is not limited to, whatever follows the word "comprising." Thus, use of the term indicates that the listed elements are required or mandatory but that other elements are optional and may or may not be present.

The term "connectable" refers to being able to be joined together for purposes including but not limited to maintaining a position, allowing a flow of fluid, performing a measurement, transmitting power, and transmitting electrical signals. The term "connectable" can refer to being able to be joined together temporarily or permanently.

A "connector" and "for connection" as used herein describes the concept of forming a fluid connection between two components wherein fluid or gas can flow from one component, through a connector or a component for connection, to another component. The connector provides for a fluid connection in its broadest sense and can include any type of tubing, fluid or gas passageway, or conduit between any one or more components of the invention.

The term "consisting of" includes and is limited to whatever follows the phrase "consisting of." Thus, the phrase indicates that the limited elements are required or mandatory and that no other elements may be present. The term "consisting essentially of" includes whatever follows the term "consisting essentially of" and additional elements, structures, acts or features that do not affect the basic operation of the apparatus, structure or method described.

A "control system" consists of combinations of components that act together to maintain a system to a desired set of performance specifications. The control system can use processors, memory and computer components configured to interoperate to maintain the desired performance specifications. The control system can also include fluid or gas control components, and solute control components as known within the art to maintain the performance specifications.

A "control valve" is a valve for controlling the movement of a liquid or a gas. When the control valve directs the movement of gas, the control valve can open or close to regulate the movement of gas from a high pressure gas source to a lower pressure.

A "controller," "control unit," "processor," or "microprocessor" is a device which monitors and affects the operational conditions of a given system. The operational conditions are typically referred to as output variables of the system wherein the output variables can be affected by adjusting certain input variables.

A "degas restrictor" is a flow restriction through which a pump pulls fluid, thereby generating a reduced pressure within the fluid flowing between the flow restriction and the pump.

A "degasser" is a component that is capable of removing dissolved and undissolved gasses from fluids. The term "degasser" can encompass a degassing vessel, and a fluid pump and a vacuum pump connected to the degassing vessel and working in concert to create a vacuum in the fluid flowing through the degassing vessel and to evacuate gas from the degassing vessel.

A "degassing flow loop" is a portion of a fluid pathway that conveys a dialysate from a dialysate flow loop to a degasser and back to the dialysate flow loop.

A "degassing membrane" is a semi-permeable membrane having a permeability coefficient selective to a particular gas such that specific gases may be removed from dialysate with particularity. The membrane may be constructed materials known in the art having the desired permeability coefficient for the targeted gas to be removed from the dialysate.

A "degassing vessel" or a "degas vessel" is a component of a degasser, and can be any structure having an inlet through which dialysate enters the vessel, a first outlet through which gas removed from the dialysate may pass, and a second outlet through which dialysate can exit the vessel once gas has been removed from the dialysate.

The term "detachable" or "detached" relates to any component of the present invention that can be separated from a system, module, cartridge or any component of the invention. "Detachable" can also refer to a component that can be taken out of a larger system with minimal time or effort. In certain instances, the components can be detached with minimal time or effort, but in other instances can require additional effort. The detached component can be optionally reattached to the system, module, cartridge or other component. A detachable module can often be part of a reusable module.

"Dialysate" is the fluid that passes through the dialyzer on the side of the dialysis membrane that is opposite to the fluid (e.g. blood) that is being dialyzed.

The term "dialysate flow loop," "dialysate flow path" or "dialysate conduit flow path" refers to any portion of a fluid pathway that conveys a dialysate and is configured to form at least part of a fluid circuit for hemodialysis, hemofiltration, ultrafiltration, hemodiafiltration or ultrafiltration. Optionally, the fluid pathway can contain priming fluid during a priming step or cleaning fluid during a cleaning step.

"Dialysis" is a type of filtration, or a process of selective diffusion through a membrane. Dialysis removes solutes of a specific range of molecular weights via diffusion through a membrane from a fluid to be dialyzed into a dialysate. During dialysis, a fluid to be dialyzed is passed over a filter membrane, while dialysate is passed over the other side of that membrane. Dissolved solutes are transported across the filter membrane by diffusion between the fluids. The dialysate is used to remove solutes from the fluid to be dialyzed. The dialysate can also provide enrichment to the other fluid.

The terms "dialysis membrane," "hemodialysis membrane," "hemofiltration membrane," "hemodiafiltration membrane," "ultrafiltration membrane," can generally be referred to as a "membrane," or can refer to a semipermeable barrier selective to allow diffusion and/or convection of solutes between blood and dialysate, or blood and filtrate, of a specific range of molecular weights in either direction through the barrier that separates blood and dialysate, or blood and filtrate, while allowing diffusive and/or convective transfer between the blood on one side of the membrane and the dialysate or filtrate circuit on the other side of the membrane.

The term "dialyzer" refers to a cartridge or container with two flow paths separated by semi-permeable membranes. One flow path is for blood and one flow path is for dialysate. The membranes can be in the form of hollow fibers, flat sheets, or spiral wound or other conventional forms known to those of skill in the art. Membranes can be selected from the following materials of polysulfone, polyethersulfone, poly(methyl methacrylate), modified cellulose, or other materials known to those skilled in the art.

A "fiber mesh" is a component made of strands of fibers with spaces between the fibers to allow fluid or gas to flow through the mesh.

"Flow" refers to the movement of a fluid or gas.

The term "flow loop" refers to a grouping of components that may guide the movement of a fluid, convey the fluid, exchange energy with the fluid, modify the composition of the fluid, measure a characteristic of the fluid and/or detect the fluid. A flow loop comprises a route or a collection of routes for a fluid to move within. Within a flow loop there may be more than one route that a volume of fluid can follow to move from one position to another position. A fluid volume may move through a flow loop such that the fluid volume recirculates, or passes the same position more than once as the fluid volume moves through a flow loop. A flow loop may operate to cause fluid volume ingress to and fluid volume egress from the flow loop. The term "flow loop" and "flow path" often may be used interchangeably.

The terms "flow restriction," "flow restriction device," "flow restrictor" and "restrictor" refer to an element or grouping of elements that resist the flow of fluid through the element or grouping of elements such that the fluid pressure within a flow stream that passes through the element or grouping of elements is greater upstream of the element or grouping of elements than downstream of the element or grouping of elements. A flow restrictor may be an active or passive device. Non-limiting examples of passive flow restriction devices are orifices, venturis, spray nozzles, a narrowing, or a simple length of tubing with flow cross section that produces the desired pressure drop when the fluid flows through the flow restrictor, such tubing being essentially rigid or compliant. Non-limiting examples of active flow restrictors are pinch valves, gate valves and variable orifice valves.

A "flow sensing apparatus" or "flow measuring apparatus" is an apparatus capable of measuring the flow of fluid or gas within a specific area.

A "fluid" is a liquid substance, optionally having a combination of gas and liquid phases in the fluid. Notably, a liquid, as used herein, can therefore also have a mixture of gas and liquid phases of matter.

The term "fluid communication" refers to the ability of fluid or gas to move from one component or compartment to another within a system or the state of being connected, such that fluid or gas can move by pressure differences from one portion that is connected to another portion.

The terms "fluidly connectable" and "fluid connection" refer to the ability of providing for the passage of fluid or gas from one point to another point. The two points can be within or between any one or more of compartments, modules, systems, components, and rechargers, all of any type.

A "fluid pump" is a pump used to move fluid throughout a system. In any embodiment, the fluid pump can create low pressure in a degassing vessel such that fluid is drawn into the degassing vessel. In any embodiment, the fluid pump can be used together with a degas restrictor. The fluid pump can work in concert with a vacuum pump to create a low pressure environment within the degassing vessel such that gas is separated from the fluid.

A "gas" is a state of matter, as opposed to liquid, solid or plasma. A gas may be comprised of elemental molecules made from one type of atom (e.g., oxygen, nitrogen), and may comprise compound molecules made from a variety of atoms (e.g., carbon dioxide). Gas may be dissolved or undissolved in a fluid, such as dialysate. At higher pressures, a greater amount of gas will remain dissolved in fluid; however, as the fluid is subjected to lower pressures, the gas will precipitate out of the fluid. In the present invention, the phrase "any other gas" refers to any gas that is not carbon dioxide that may be found in dialysate or any other fluid used in dialysis, such as nitrogen and oxygen.

A "gear pump" is a pump that uses the meshing of gears to create a pressure to displace fluid, gas or both.

The term "hydrophobic membrane" refers to a semipermeable porous material that may allow gas phases of matter to pass through the membrane, but which substantially resists the flow of liquid water through the membrane due to the surface interaction between the liquid water and the hydrophobic material of the membrane.

A "level sensor" is a component capable of determining the level of a fluid in a container. The terms "upper level sensor" and "lower level sensor" refer to the respective positions of level sensors.

The term "particle filter" refers to a device configured to inhibit the passage particulate matter conveyed by a fluid or solution while allowing the passage of the fluid or solution.

A "narrowing" is a portion of a fluid flow path having a smaller interior diameter than a portion of a fluid flow path immediately adjacent to the narrowing in any direction of fluid flow. The portions adjacent to the narrowing having a larger diameter can occur either before or after, and in some cases before and after the narrowing. All rates at which the diameter of the narrowing can be reduced relative to adjacent portions or to the degree to which a flow path can be narrowed, are contemplated by the present definition.

A "nucleation chamber" is a device containing a high surface area medium, such as a filter, fiber mesh, or beads onto which gases can nucleate to form bubbles.

An "operational line" or "line" is a passageway, conduit or connector that directs fluid or gas in a path used while the system is in operation.

An "overflow float" is a component in a degassing vessel that serves to keep liquid from moving through the gas vent port in the degassing vessel. The overflow float has a density less than that of water. As the liquid level in the degassing vessel rises, the overflow float will float on top of the liquid, eventually coming into contact with, and blocking the vent.

The terms "pathway," "conveyance pathway," "fluid flow path," and "flow path" refer to the route through which a fluid or gas, such as dialysate or blood travels.

A "patient" or "subject" is a member of any animal species, preferably a mammalian species, optionally a human. The subject can be an apparently healthy individual, an individual suffering from a disease, or an individual being treated for a disease.

The term "peristaltic pump" refers to a pump that operates by compression of a flexible conduit or tube through which the fluid to be pumped passes.

The term "physiologically compatible fluid" or "physiologically compatible solution" refers to a fluid that can be safely introduced into the bloodstream of a living subject.

The terms "pressure meter" and "pressure sensor" refer to a device for measuring the pressure of a gas or fluid in a vessel or container.

The term "pulsatile pump" refers to a pump wherein the pumped fluid undergoes periodic variation in velocity and/or pressure.

The term "pump" refers to any device that causes the movement of fluids or gases by the application of suction or pressure.

The terms "pump rate" and "volumetric pumping rate" refer to the volume of fluid that a pump conveys per unit of time.

A "recirculating flow path" is a flow path configured such that fluid or gas within the flow path can pass by the same point in the flow path more than one time.

A "sensor" is a component capable of determining the states of one or more variables in a system.

The term "ultrafiltrate" refers to fluid that is removed from a subject by convection through a permeable membrane during hemodialysis, hemofiltration, hemodiafiltration, or peritoneal dialysis. The term "ultrafiltrate," as used herein, can also refer to the fluid in a reservoir that collects fluid volume removed from the patient, but such a reservoir may also include fluids or collections of fluids that do not originate from the subject.

The term "undissolved gases" refers to gases that are not part of a solution, including free gases or bubbles. By contrast, "dissolved gases" include gases dissolved in a liquid such as water or dialysate.

A "vacuum pump" is a pump used to create negative pressure in a degassing vessel and remove gas from the vessel.

A "valve" is a device capable of directing the flow of fluid or gas by opening, closing or obstructing one or more pathways to allow the fluid or gas to travel in a particular path. One or more valves configured to accomplish a desired flow can be configured into a "valve assembly."

A "vent valve" is a valve that controls the movement of a gas into and out of a vent. A "mechanical vent valve" is a vent valve that is opened or closed based on an external component, such as an overflow float, blocking or not blocking the mechanical vent valve.

The term "vent" as referred to in relationship to a gas, refers to a means for permitting the escape of a gas from a defined portion of the system, such as, for example, would be found in the degassing module.

A "vent line" is a passage for fluid, gas, or mixtures thereof, wherein the passage can be fluidly connectable to a vent.

Degassing Module

The first, second and third aspects of the invention relate to a degasser and related systems and methods for removing gas, and specifically carbon dioxide, generated from the breakdown of urea in the sorbent cartridge. A degassing module in accordance with the first, second and third aspects of the invention is shown in FIG. 1a. The direction of dialysate flow is shown by the arrows. In any embodiment of the first, second and third aspects of the invention, the degassing module can be placed in the dialysis circuit preferably at a point between the sorbent cartridge (not shown) and the dialyzer (not shown). The degassing module can have a degassing flow loop providing fluid flow that is in parallel to the dialysate flow loop. In any embodiment of the first, second and third aspects of the invention, the parallel configuration allows the fluid flow through the degassing loop to be independent of the fluid flow rate through the dialyzer such that the fluid flow rate through the degassing loop can be either less than or greater than the dialysate flow rate through the dialyzer. Thus, the parallel configuration provides control flexibility to adjust the degassing loop flow rate for optimal degassing without requiring the dialysate flow rate through the dialyzer to change. Alternatively, in any embodiment of the first, second and third aspects of the invention, the fluid flow through the degassing module can be arranged in series with the dialysate flow to the dialyzer.

As the dialysate enters the degassing module, the dialysate can pass a degas restrictor 13 of FIG. 1a. The degas restrictor 13 can serve to restrict the flow of fluid through the degassing system. In any embodiment of the first, second and third aspects of the invention, the degas restrictor 13 may be a narrow tube or any portion of the flow path that can be narrowed in a controlled fashion. For example, restriction can be provided by a portion of the flow path being crushable and having roller portions to create a portion of the flow path having a narrowed inner diameter to thereby restrict flow. Any other mechanical structures known to those of ordinary skill to restrict flow is also contemplated by the first, second and third aspects of the invention. The fluid pump 12, fluidly connected to the degas restrictor 13, pulls fluid through the degas restrictor 13, creating a reduced pressure in the degassing vessel 11 side of the degas restrictor 13. In any embodiment of the first, second and third aspects of the invention, a vacuum can be created in the degassing vessel 11 side of the degas restrictor 13. In any embodiment of the first, second and third aspects of the invention, a pressure sensor (not shown) can be placed after the degas restrictor 13 to determine the pressure of fluid in the degasser. Importantly, the fluid pump 12 of the present invention can be located downstream of the degassing vessel 11 to allow for improved removal of carbon dioxide. The vacuum that can be created by pulling the fluid through the degas restrictor 13 helps to draw dissolved gases, including carbon dioxide, out of solution by reducing the pressure of the fluid below the partial pressure of the dissolved gas in the liquid. In any embodiment of the first, second and third aspects of the invention, the degas restrictor need not be a separate component. Instead, the fluid inlet of the degassing vessel 11 can be narrow, and therefore operate as a flow restrictor. Vacuum pump 14 on the gas removal pump assembly 15 can be fluidly connected to the degassing vessel 11 by gas removal line 23 and can desirably remove the gases in the low pressure environment inside degassing vessel 11 via mechanical vent valve 20. The fluid enters the degas vessel 11, by crossing through the base 25 of the degassing vessel 11 and through degas sprayer 18. However, there is no particular requirement of the first, second or third aspects of the invention for the fluid to enter or exit through the base. The degas sprayer 18 creates a thin spray or mist, which can increase release of dissolved gases from solution by increasing the surface area of liquid in contact with the low pressure atmosphere in the gas space 21 inside degassing vessel 11 to increase the rate at which gas can be liberated from the liquid. In any embodiment of the first, second and third aspects of the invention, the fluid can enter the degas vessel 11 at other locations than the base 25. For example, fluid can enter the degas vessel 11 at a location on the side of the degas vessel 11. The degas sprayer 18 can be positioned within the degassing vessel 11 so that the degas sprayer 18 is above the maximum fluid level 26. In any embodiment of the first second and third aspects of the invention, the degas sprayer 18 is optional and not required to remove carbon dioxide or other gases from the dialysate solution. In any embodiment of the first, second and third aspects of the invention, flow restrictions in degas sprayer 18 cause sufficient pressure reduction in the fluid and degas restrictor 13 is not required. Carbon dioxide and other gases collect in the gas collection area 21 of the degassing vessel 11 and leave the degassing vessel 11 through vent valve 10, positioned on a connector 33 fluidly connected to the degassing vessel 11. Although depicted as a 3-way valve, vent value 10 can be any combination of one or more valves suitable for accomplishing the desired control of gas flow. In FIG. 1*a*, the pathways open in valve 10 are shown in black. Vacuum pump 14 on the gas removal pump assembly 15 is attached to the degas vessel 11 by gas removal line 23, and provides the force necessary to move gases from the lower pressure degassing vessel 11 out into the atmosphere. The vacuum pump 14 exerts a vacuum that is greater than or equal to the vacuum created by the liquid pump 12 pulling fluid through the restrictor 13, which allows the removal of the accumulated gas from the degassing vessel 11.

The degassing vessel 11 of the first, second and third aspects of the invention can be operated at a pressure lower than atmospheric pressure due to the presence of vacuum pump 14. By maintaining the degassing vessel 11 at a pressure less than atmospheric pressure, carbon dioxide present in the fluid can be more easily removed than in the absence of the described system of pumps of the first, second and third aspects of the invention. In any embodiment of the first, second and third aspects of the invention, the vent valve 10 can allow gas to leave directly into the atmosphere through vent valve filter 29, as represented by arrow 30. The vent valve filter 29 is a particle filter that serves to remove particulate matter from air flowing through filter 29. In any embodiment of the first, second and third aspects of the invention, the gases may travel through degas line 23, to the gas removal pump assembly 15 and into the atmosphere as represented by arrow 24.

Vent valve 10 can be a three way valve, as shown in FIG. 1*a*. This can allow air to be removed from the degas vessel 11 through the degas line 23, and also allow air to be drawn into the degas flow loop when fluid is being drained from the system. Overflow float 19 and mechanical vent valve 20 can provide a mechanism for an automatic shutdown, preventing fluid from leaving the degassing vessel 11 through the vent valve 10, but allowing air to be added or removed during filling or draining of the system. If the fluid level in the degassing vessel 11 reaches above a certain point, overflow float 19 can block, either directly or indirectly, the fluid from passing through mechanical vent valve 20. The maximum fluid level in the degas vessel 11 can be shown by line 26, while the minimum fluid level can be shown by line 22. In any embodiment of the first, second and third aspects of the invention, a degas float channel 27 can be used to ensure that the overflow float 19 properly engages with the mechanical vent valve 20. The degas float channel 27 can be placed directly underneath the mechanical vent valve 20 so that when the overflow float 19 rises to the top of the degas chamber 11, the overflow float 19 will properly cover the mechanical vent valve 20. Alternatively, the float can move an actuator so that the mechanical vent valve 20 is closed. The degas float channel 27 can be made with a fluid permeable substance, such as mesh, so that fluid can still move freely through the degas vessel 11. In any embodiment of the first, second and third aspects of the invention, the function of the degas float channel 27 can be accomplished by a rod through the overflow float 19 wherein the rod is anchored to the degassing vessel 11. In any embodiment of the first, second and third aspects of the invention, the overflow float 19 can be tethered to actuators (not shown). If the overflow float 19 rises, the tethers (not shown) can activate the actuators by pulling on the actuators to either shut off, or modulate the pump rate of, the vacuum pump 14 and fluid pump 12.

Lower level sensor 17 and upper level sensor 16 can sense the fluid level in the degassing vessel 11. The fluid level in the degassing vessel 11 can be a function of the vacuum created by fluid pump 12 and vacuum pump 14 working independently or in concert. The pump rate of the fluid pump 12 and vacuum pump 14 can be adjusted as necessary to maintain the correct fluid level in the degassing vessel 11. In any embodiment of the first, second and third aspects of the invention, the lower level sensor 17 and upper level sensor 16 can be in electronic communication with a control system (not shown). The pump rates of the fluid pump 12 and vacuum pump 14 can be automatically adjusted by the control system to maintain the proper level of fluid in the degas vessel 11. If the fluid level in the degas vessel 11 is near or above the maximum fluid level 26, the pump rates of the fluid pump 12 can be increased, and/or vacuum pump 14 can be reduced. If the fluid level in the degas vessel 11 is near or below the minimum fluid level 22, the pump rates of the fluid pump 12 can be reduced and/or vacuum pump 14 can be increased.

In any embodiment of the first, second and third aspects of the invention, only one sensor is necessary to detect the fluid level in the degassing vessel 11. For example, an ultrasonic sensor or mechanical float can be used to determine the fluid level in the degassing vessel 11. Any other type of fluid level sensor known in the art is contemplated by the first, second and third aspects of the invention.

Carbon dioxide sensor 28 can determine the amount of carbon dioxide present in the dialysate flow loop after dialysate has passed through the degasser. The pump rates of fluid pump 12 and vacuum pump 14 can be adjusted as discussed below in response to signals received from the carbon dioxide sensor 28 in order to remove more or less carbon dioxide from the dialysate, and therefore deliver more or less carbon dioxide to the main dialysate flow path. In any embodiment of the first, second and third aspects of the invention, the pumps can be adjusted automatically if the level of carbon dioxide detected in the dialysate by carbon dioxide sensor 28 is higher or lower than a pre-set value. In any embodiment of the first, second and third aspects of the invention, the pumps can be adjusted manually in response to output from the carbon dioxide sensor 28. In any embodiment of the first, second and third aspects of the invention, the optimum carbon dioxide concentration in the fluid after passing through the degasser can be between any of 50 and 200 mmHg partial pressure, 50 and 120 mmHg partial pressure, 50 and 80 mmHg partial pressure, 70 and 100 mmHg partial pressure, 80 and 120 mmHg partial pressure, 50 and 200 mmHg partial pressure, or 100 and 200 mmHg partial pressure. The carbon dioxide sensor 28 can be placed anywhere in the dialysate flow loop, but preferably between the outlet of the degassing flow path and the inlet of the dialyzer (not shown).

Carbon dioxide sensors and sensors are known in the art. Examples include non-dispersive infrared (NDIR) detectors that detect carbon dioxide concentration in a gas and which are commercially available from a number of manufacturers, for example Gas Sensing Solutions, Glasgow Scotland; colormetric optical detectors that detect carbon dioxide in a liquid by means of a substrate that produce color change when the concentration of carbon dioxide in the liquid changes (PreSens Precision Sensing GmbH, Regensburg Germany); and sensors that utilize Severinghaus electrodes, such as the InPro $CO_2$ sensor from Mettler Toledo, Leicester England.

The pumps of the degassing module can be of any type known in the art. In any embodiment of the first, second and third aspects of the invention, fluid pump 12 and vacuum pump 14 can be the same type of pump. In any embodiment of the first, second and third aspects of the invention, fluid pump 12 and vacuum pump 14 may be different types of pumps. In any embodiment of the first, second and third aspects of the invention, the fluid pump 12 and vacuum pump 14 can be a gear pump. In any embodiment of the first, second and third aspects of the invention, fluid pump 12 and vacuum pump 14 can be a peristaltic pump, a diaphragm pump or an impeller pump. In any embodiment of the first, second and third aspects of the invention, fluid pump 12 can also have a sensor 31 attached to the pump 12 to monitor performance of the pump 12 and detect wear. In any embodiment of the first, second and third aspects of the invention, the fluid pump 12 must be selected for operating with the pump inlet at a low absolute pressure necessary to efficiently remove carbon dioxide.

Flow of fluid through the degassing module can be variable. Control over the flow can be provided by fluid pump 12. Under certain operating conditions the flow rate provided by fluid pump 12 can be less than the flow rate through the main dialysate loop. In any embodiment of the first, second and third aspects of the invention, fluid pump 12 can be operated so that flow through the degassing module is significantly greater than flow through the main dialysate loop. In any embodiment of the first, second and third aspects of the invention, the fluid pump 12 can be operated to move fluid through the degassing flow loop at a rate of 2-3 times that of the dialysate flow loop. In any embodiment of the first, second and third aspects of the invention, the fluid pump 12 can be operated to move fluid through the degassing flow loop at a rate between 1-6 times that of the dialysate flow loop, 1-2 times that of the dialysate flow loop, 3-4 times that of the dialysate flow loop, 4-5 times that of the dialysate flow loop or 5-6 times that of the dialysate flow loop. In any embodiment of the first, second and third aspects of the invention, the flow through the degassing module can be controlled automatically depending on the amount of carbon dioxide that is to be removed.

The first, second and third aspects of the invention can utilize the vacuum pump 14 to remove gas from the degassing vessel 11 to the atmosphere when the degassing vessel is operated under vacuum. Known degassing systems pump fluid into a vessel at ambient pressure where bubbles are allowed to escape. However, providing a second pump or any one of the specific pump configurations described in the first, second and third aspects of the invention to keep a degassing vessel under vacuum can unexpectedly result in higher amount of gases such as carbon dioxide being removed.

In any embodiment of the first, second and third aspects of the invention, the passage from the degassing vessel 11 to valve 10 can be covered by a hydrophobic membrane (not shown). A hydrophobic membrane will prevent fluid from escaping the degassing vessel 11 through vent opening 20. This, in turn, protects the vacuum pump 14 from being damaged by liquid and prevents undesired loss of liquid from the system while still enabling gas to be removed. In any embodiment of the first, second and third aspects of the invention, the hydrophobic membrane can be positioned in any appropriate location to guard against inadvertent fluid flow to the vacuum pump 14, and thereby prevent fluid damage. One example of a hydrophobic membrane is Polytetrafluoroethylene, or PTFE. However, the hydrophobic membrane can be made of any material.

Figure 1B:
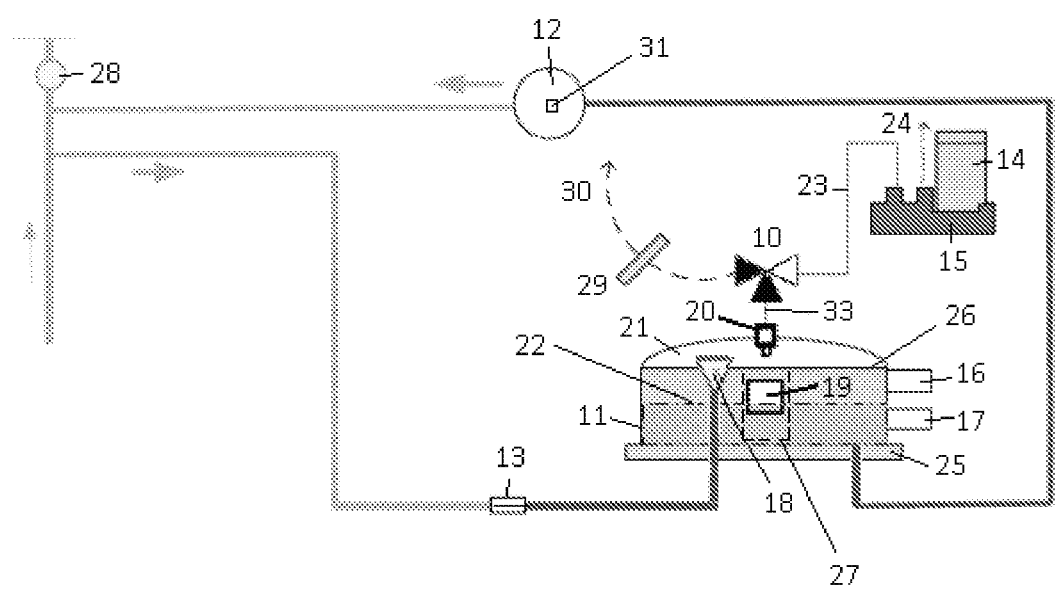
FIG. 1b shows a schematic of a degassing module for use in sorbent dialysis configured to allow air to be drawn into the system.

During draining of the dialysis system of the first, second and third aspects of the invention, air can be drawn into the system in order to drain out the fluid in the fluid pathways of the system. Air can be added to the system through valve 10 as shown in FIG. 1b. In FIG. 1b, the pathways of valve 10 that are open are shown in black. Air can be passed through filter 29, which can remove any particulate matter and microorganisms before the air enters the dialysis system, and into the degassing vessel 11 through vent 10. Fluid pump 12 can force this air into the dialysate flow loop (not shown).

Figure 2:
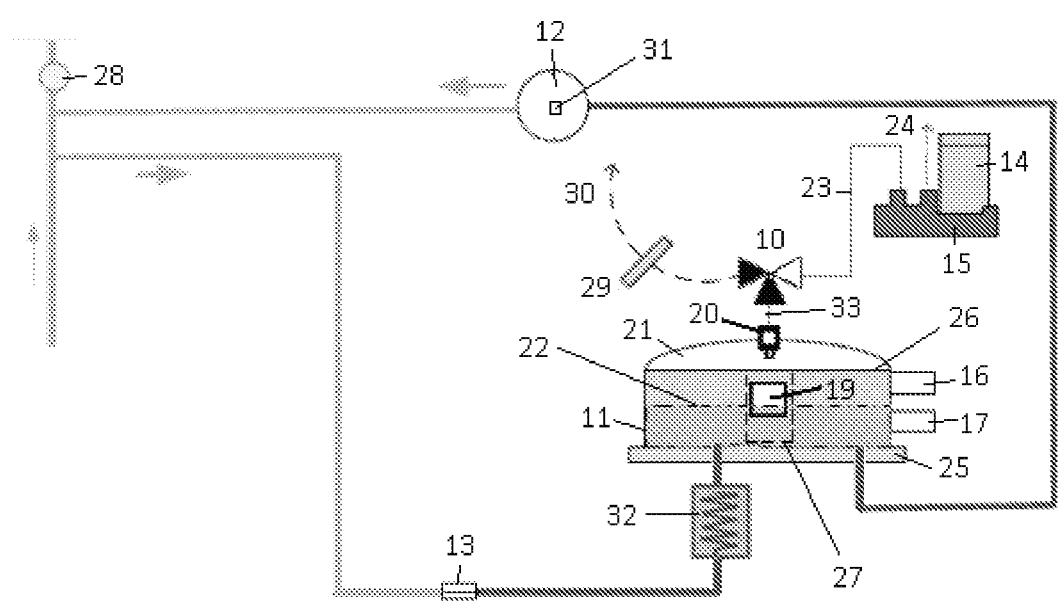
FIG. 2 shows a schematic of a degassing module for use in sorbent dialysis configured to degas dialysate utilizing a nucleation chamber.

In any embodiment of the first, second and third aspects of the invention, as shown in FIG. 2, the function of the degas sprayer can be replaced by a nucleation chamber 32. Nucleation chamber 32 contains a high surface area medium, such as fiber mesh, filter or beads, or other configuration known to those of ordinary skill. The high surface area provides sites where gas bubbles can nucleate and collect to form larger bubbles, making removal of the gases more efficient. The bubbles rise through the fluid as the fluid enters the degas vessel 11 and collect at the gas collection area 21, similar to what is shown in FIG. 1a. In any embodiment of the first, second and third aspects of the invention, the nucleation chamber 32 can be placed inside of the degas vessel 11, so that fluid moves through the nucleation chamber 32 as the fluid moves through the degas vessel 11 and gas bubbles, once freed from the high surface area medium in the nucleation chamber 32, are immediately collected in the gas collection area 21 of the degas vessel 11.

In any embodiment of the first, second and third aspects of the invention, both a nucleation chamber and a degas sprayer can be used. Such an arrangement can further help gas to be released from solution to collect at the top of the degas vessel 11. In any embodiment of the first, second and third aspects of the invention, only one of a degas sprayer or nucleation chamber can be used.

Figure 3:
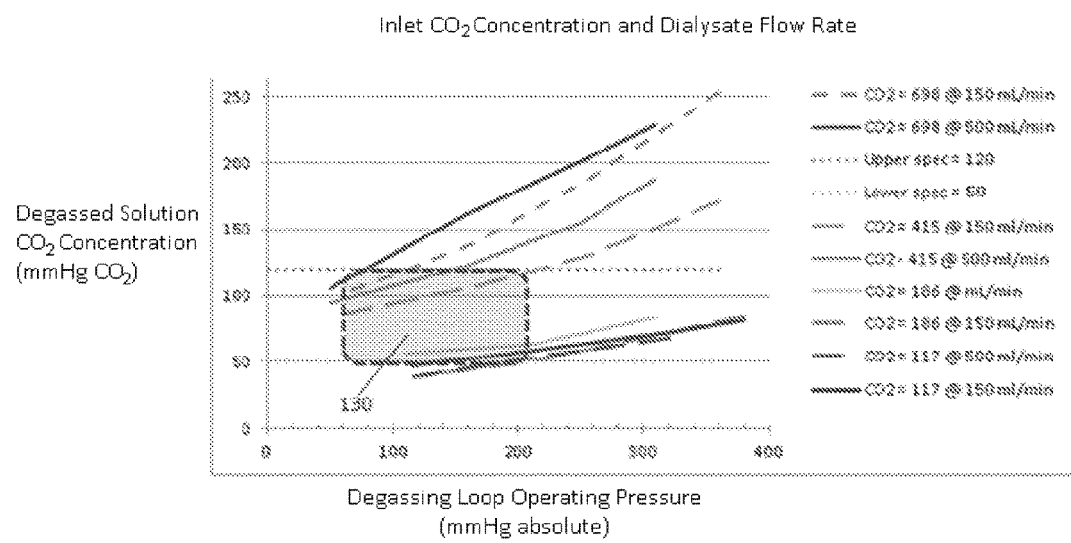
FIG. 3 is a graph showing the outlet $CO_2$ concentration in a degasser as a function of the absolute pressure in the degassing vessel.

FIG. 3 is a graph showing the $CO_2$ outlet concentration, stated as partial pressures, at the outlet of the degasser as a function of the absolute pressure in the degassing vessel for a variety of $CO_2$ inlet concentrations, stated as partial pressures. The block labeled 130 is a desired operating $CO_2$ concentration, expressed as a partial pressure, of between 50 and 120 mmHg. The absolute pressure in the degassing vessel 11 shown in FIGS. 1 and 2 is a function of the fluid pressure, determined by the pump rate of the fluid pump 12, and the vacuum pressure, determined by the pump rate of the vacuum pump 14. By controlling the two pumps, the pressure in the degassing vessel 11 can be accurately controlled. As shown in FIG. 3, the degasser of the first, second and third aspects of the invention is capable of removing enough $CO_2$ to generate a $CO_2$ concentration at the outlet of the degasser between 50 and 120 mmHg for a large range of inlet $CO_2$ concentrations and dialysate flow rates. In any embodiment of the first, second and third aspects of the invention, a degassing vessel pressure of between 60 and 200 mmHg absolute pressure can allow for optimal $CO_2$ removal across a range of inlet $CO_2$ concentrations and dialysate flow rates. In any embodiment of the first, second and third aspects of the invention, a degassing vessel pressure of between any of 40 mmHg and 2000 mmHg, 40 mmHg and 300 mmHg, 40 mmHg and 100 mmHg, 80 mmHg and 150 mmHg, 120 mmHg and 250 mmHg or 200 mmHg and 300 mmHg, can allow for optimal $CO_2$ removal. The desired outlet concentration of $CO_2$ can be obtained for the entire range of inlet $CO_2$ concentrations and flow rates tested by adjusting the pump rates of the two pumps to arrive at the necessary degassing vessel pressure. In any embodiment of the first, second or third aspects of the invention, the vacuum pump may be shut off if the $CO_2$ concentration is below the lower limit. In such cases, the pressure in the degassing vessel will be the same as the pressure of the dialysate fluid, which can be up to 2000 mmHg.

Figure 4:
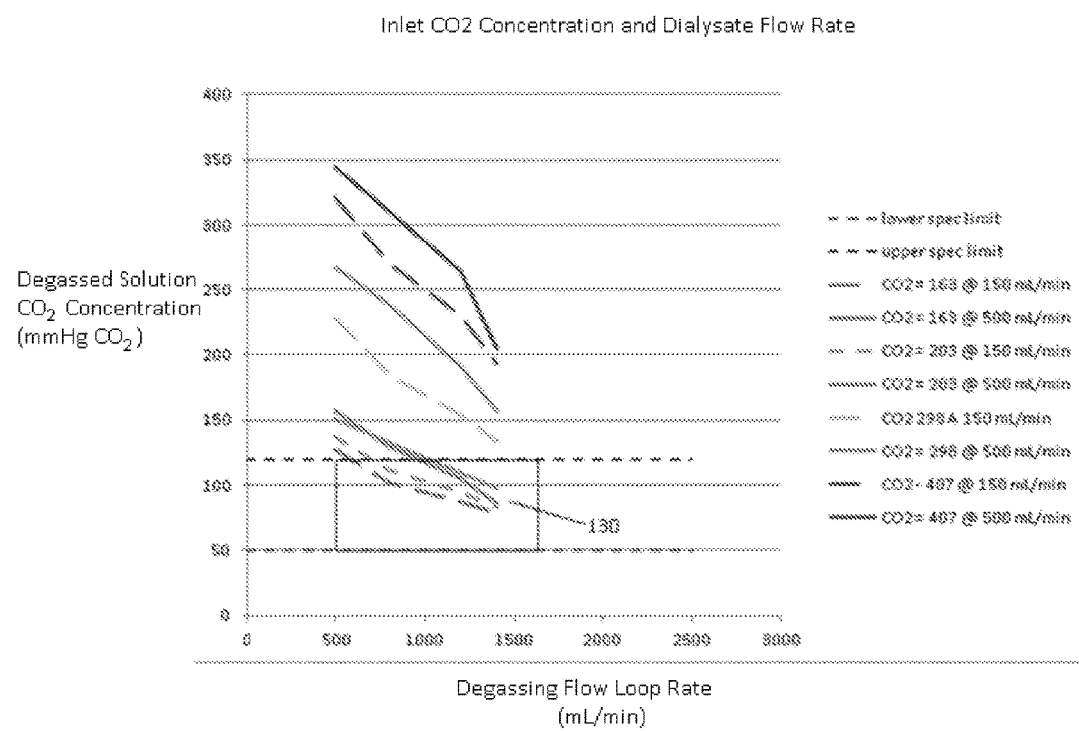
FIG. 4 is a graph showing the outlet $CO_2$ concentration in a degasser as a function of the flow rate in a system with a degasser at ambient pressure.

FIG. 4 provides comparative data for known systems operating at ambient pressures showing an outlet $CO_2$ concentration, stated as partial pressure, in a system that does not use a vacuum pump as in the first, second and third aspects of the invention. Because no vacuum pump is used in known systems, and the known degassing vessels are not able to operate at low absolute pressures, the amount of $CO_2$ removed is limited by the need to maintain sufficient pressure in the degassing vessel to vent the released gas. As can be seen in FIG. 4, a degasser without a degassing vessel under vacuum can only operate to obtain an outlet $CO_2$ concentration of between 50 and 120 mmHg when the inlet concentration of $CO_2$ is around 200 mmHg or below.

Figure 5A:
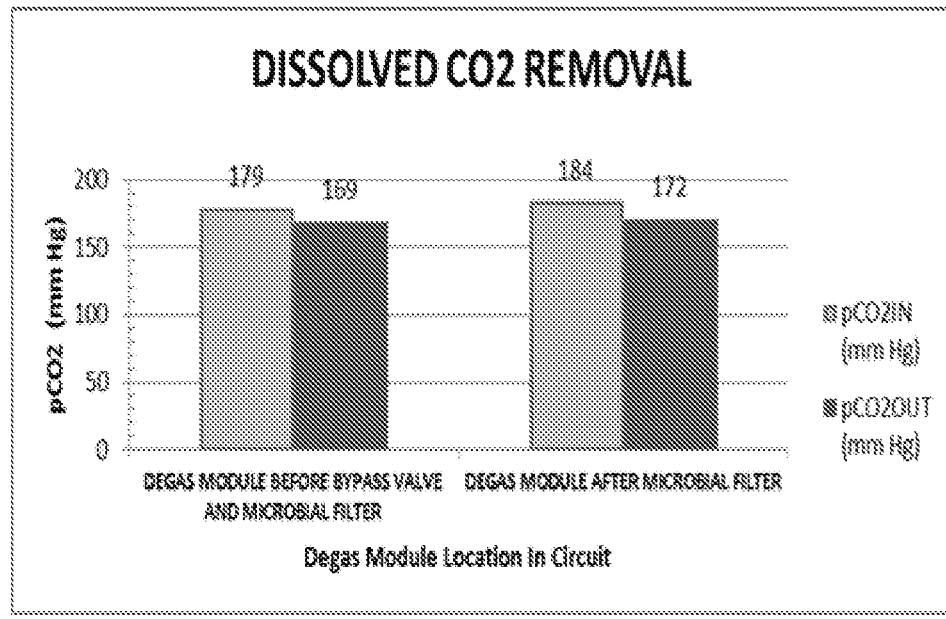
FIG. 5a is a graph showing the amount of dissolved $CO_2$ removed by a degasser with a fluid pump upstream of the degassing vessel for two locations in a dialysis circuit.
Figure 5B:
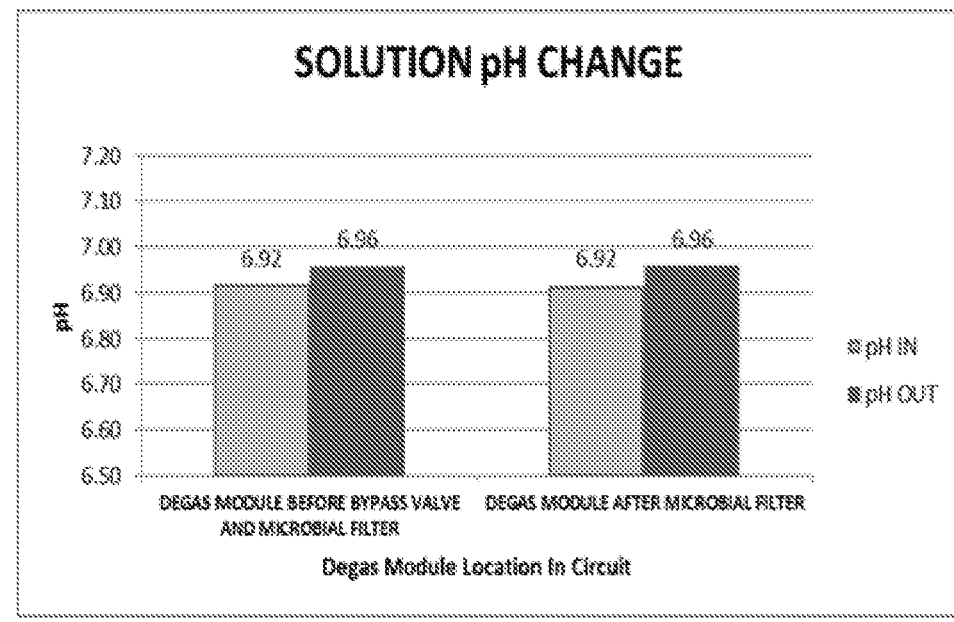
FIG. 5b is a graph showing the change in pH of a fluid passing through a degasser with a fluid pump upstream of the degassing vessel for two locations in a dialysis circuit.
Figure 6A:
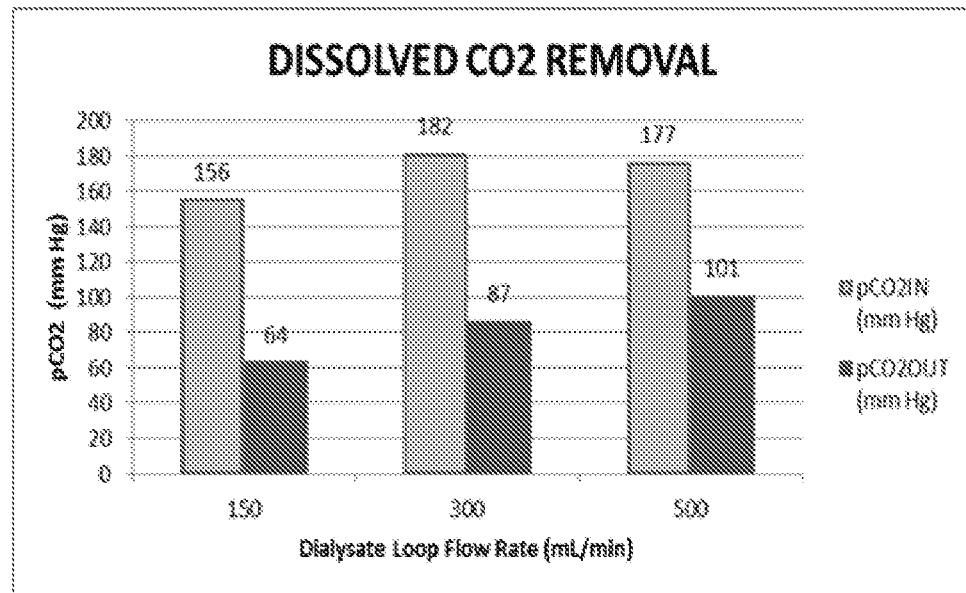
FIG. 6a is a graph showing the amount of dissolved $CO_2$ removed by a degasser with a fluid pump downstream of the degassing vessel as a function of the dialysate flow loop flow rate.
Figure 6B:
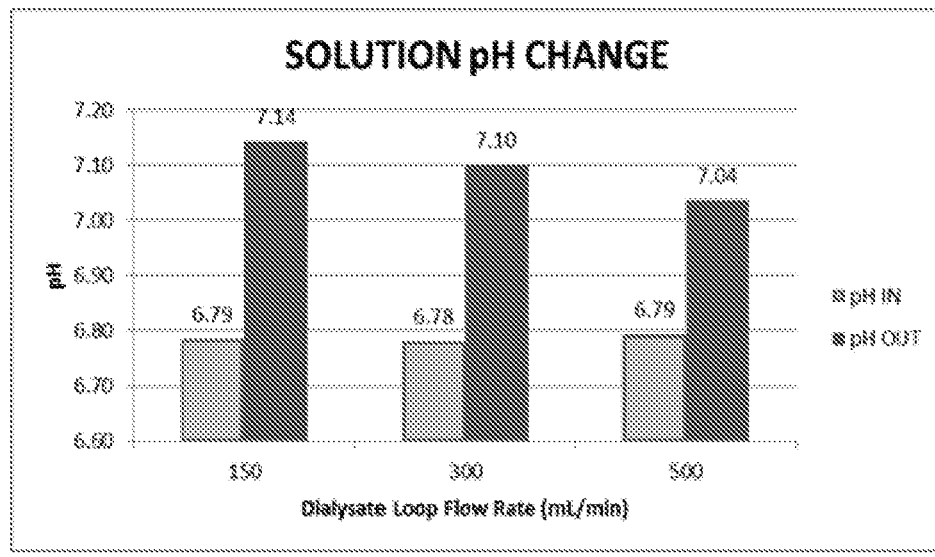
FIG. 6b is a graph showing the change in pH of a fluid passing through a degasser with a fluid pump downstream of the degassing vessel as a function of the dialysate flow loop flow rate.

As shown in FIGS. 5 and 6, the addition of the fluid pump downstream from the degassing vessel can be important to the first, second and third aspects of the invention. By placing the fluid pump downstream of the degas vessel, the efficiency of removing $CO_2$ was increased. FIG. 5a shows the amount of $CO_2$ removed from dialysate without operating the degas vessel under vacuum by means of a fluid pump placed downstream of the degas vessel. FIG. 5b shows the change in pH in the same system. By contrast, FIGS. 6a and 6b show the amount of $CO_2$ removed, and the effect on pH, in the same system with a fluid pump added downstream of a degassing vessel, shown for a dialysate flow loop flow rate from 150 mL/min to 500 mL/min. As can be seen in FIGS. 6a and 6b, by adding the fluid pump to a downstream location, between ⅓ and ⅔ of $CO_2$ can be removed, depending on the dialysate flow rate. By contrast, as shown in FIGS. 5a and 5b, much less $CO_2$ is removed when the fluid pump is placed upstream of a degas vessel.

As can be seen in FIG. 5, the location of the degasser upstream or downstream with respect to a microbial filter does not alter the amount of $CO_2$ removed. The described configuration with degasser upstream of the microbial filter can provide for the removal of gas from the dialysate prior to reaching the microbial filter, and thereby advantageously reduce gas accumulation in the microbial filter.

Figure 7:
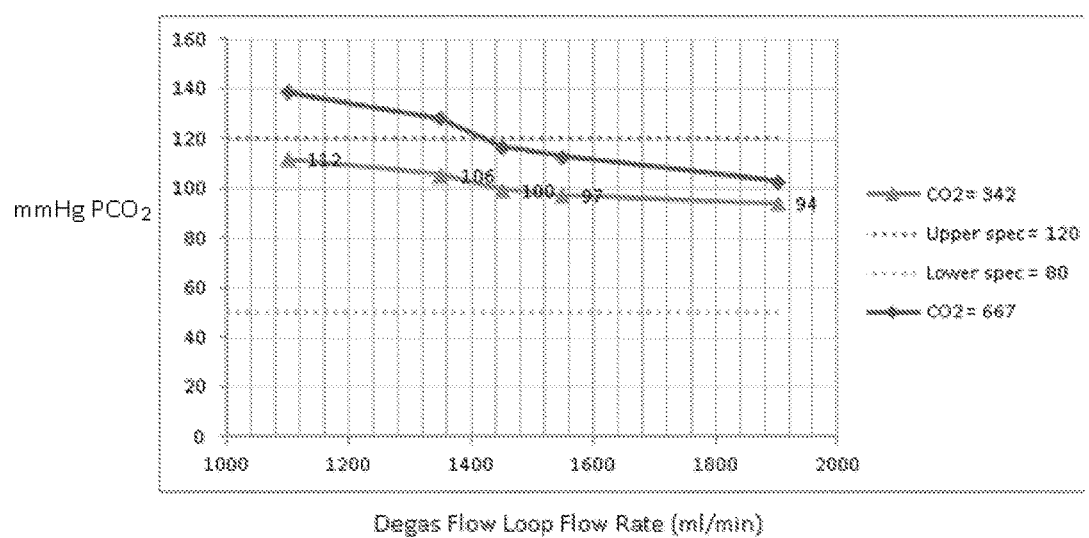
FIG. 7 is a graph showing the amount of dissolved $CO_2$ removed by a degasser with a fluid pump downstream of the degassing vessel as a function of the degassing flow loop flow rate.

FIG. 7 shows the amount of $CO_2$ removed as a function of the rate of flow through the degassing flow loop. In all runs shown in FIG. 7 the dialysate flow rate was 600 mL/min. As is shown, the amount of CO2 removed can increase as the flow rate through the degassing flow loop increases.

Figure 8A:
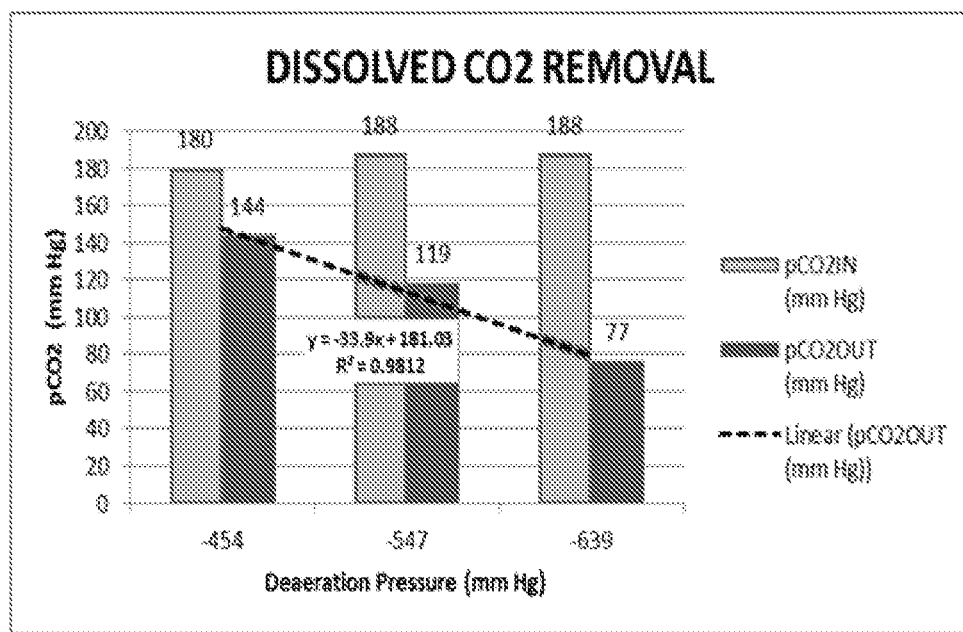
FIG. 8a is a graph showing the amount of dissolved $CO_2$ removed by a degasser with a fluid pump downstream of the degassing vessel as a function of the vacuum level in the degassing flow loop.
Figure 8B:
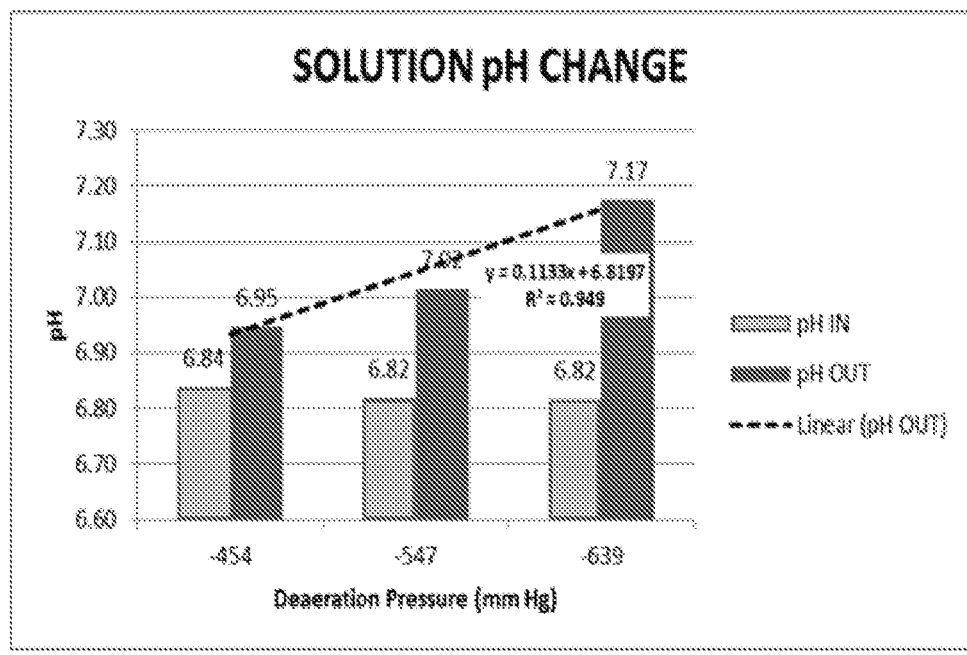
FIG. 8b is a graph showing the change in pH of a fluid passing through a degasser with a fluid pump downstream of the degassing vessel as a function of the vacuum level in the degassing flow loop.

FIGS. 8a and 8b show the amount of $CO_2$ removed, and the effect on pH, as a function of the absolute pressure in the degassing flow loop. In these trials, the dialysate flow rate and degassing flow rate were held constant at 300 mL/min. As can be seen, more $CO_2$ is removed as the absolute pressure in the degassing flow loop is reduced. As is shown in FIGS. 8a and 8b, the degassing flow loop pressure can have a linear relationship with outlet $CO_2$ concentration. The pressure in the degassing flow loop, and in the degas vessel in particular, can be affected by the action of the fluid pump pulling fluid through the degas flow restrictor and the vacuum pump acting to remove the released gases from the degassing vessel. The action of the vacuum pump allows released gases to be vented from the degas vessel when the degas vessel is operated at pressures substantially below ambient. This, in turn, can allow for the removal of additional $CO_2$.

Figure 9A:
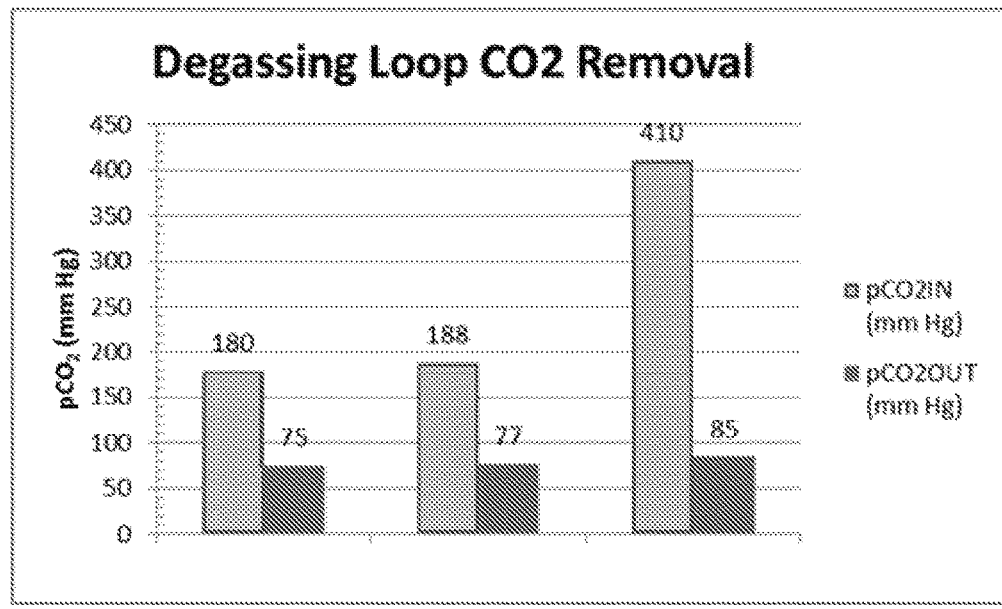
FIG. 9a is a graph showing the amount of dissolved $CO_2$ removed by a degasser with a fluid pump downstream of the degassing vessel as a function of the $CO_2$ concentration at the inlet of the degasser.
Figure 9B:
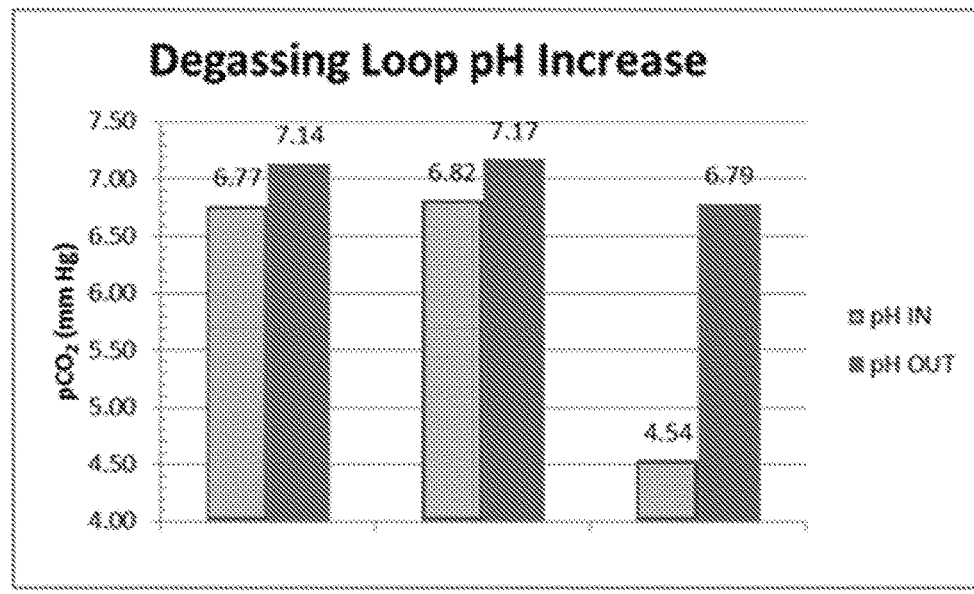
FIG. 9b is a graph showing the change in pH of a fluid passing through a degasser with a fluid pump downstream of the degassing vessel as a function of the pH at the inlet of the degasser.

The outlet $CO_2$ concentration can be dependent on the inlet $CO_2$ concentration, the fluid pressures within the degassing flow loop, and the rates of flow through dialysate flow loop and the degassing flow loop. In any embodiment of the first, second and third aspects of the invention, the dialysate flow loop and the degassing flow loop can operate in parallel or in series. FIGS. 9a and 9b show the amount of $CO_2$ removed, and the effect on pH with differing inlet $CO_2$ concentrations. In all trials, the flow rates through the dialysate flow loop and degassing flow loop were held at 300 mL/min and the degassing loop fluid pressure was held constant at 630 mmHg vacuum. As can be seen, the outlet $CO_2$ concentration is not significantly affected by large changes in the inlet $CO_2$ concentration. In all cases, the outlet $CO_2$ concentration was reduced to between 75-85 mmHg, despite the variations in inlet $CO_2$ concentrations.

Figure 10:
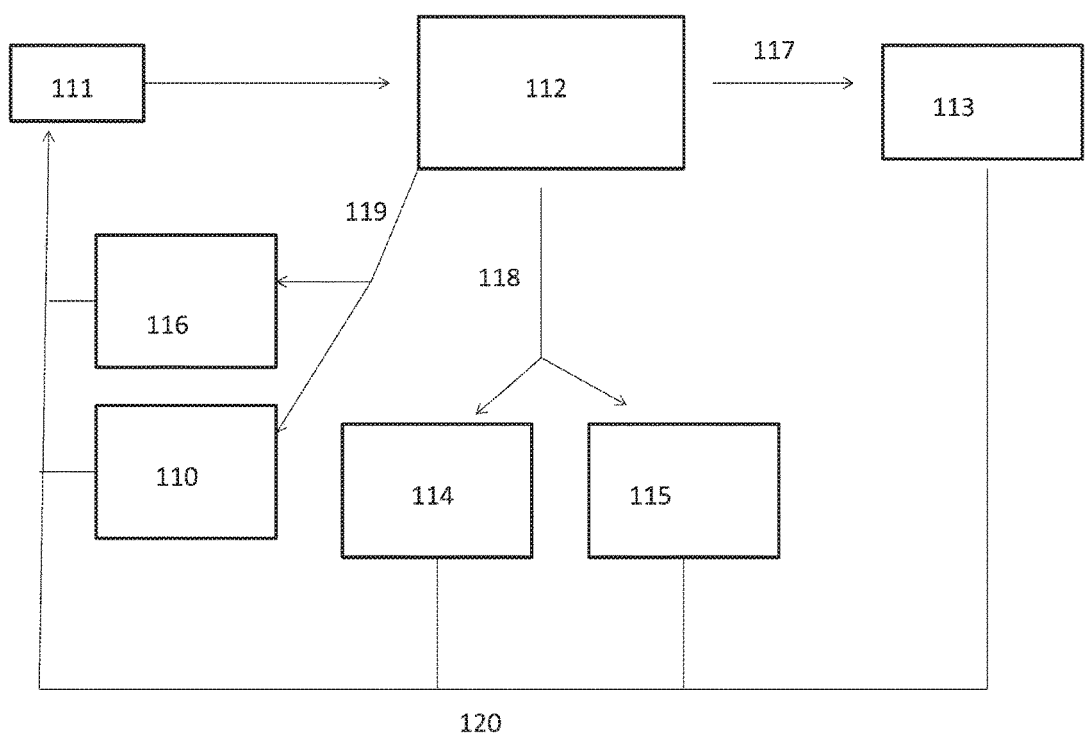
FIG. 10 is a flow diagram showing the operation of the pumps in relation to the carbon dioxide present in the dialysate.

FIG. 10 shows a flow diagram, explaining one non-limiting embodiment of the operation of the vacuum pump and fluid pump of the first, second and third aspects of the invention in relation to the data received from the $CO_2$ sensor. In FIG. 10, both the vacuum pump and the liquid pump may be operated simultaneously. Data received from the $CO_2$ sensor 111 is transmitted to control unit 112. If the $CO_2$ concentration detected by the $CO_2$ sensor is within the desired range 117, the control unit 112 can continue operating the pumps in the same manner 113. If the $CO_2$ concentration detected by the $CO_2$ sensor is too low 118, the control unit can do either of two options. The control unit can cause the fluid pump to decrease the flow rate in the degassing flow loop 114, causing the absolute pressure of the fluid in the degassing loop to increase and thereby reduce the amount of $CO_2$ removed by the degasser as shown in FIGS. 3 and 7. In any embodiment of the first, second and third aspects of the invention, step 114 can alternatively involve that the fluid pump is shut off completely, thereby stopping the removal of $CO_2$ from the dialysate. Alternatively, the control unit can decrease the pump rate of, or shut off completely, the vacuum pump 115. In any embodiment of the first, second and third aspects of the invention, both steps 114 and step 115 can be carried out in response to a signal showing the $CO_2$ level to be too low. Decreasing the pump rate of the vacuum pump, or shutting the vacuum pump off completely, will result in less gas being removed from the degas vessel. If the $CO_2$ concentration detected by the $CO_2$ sensor is too high 119, the control unit can cause the fluid pump to increase the flow rate through the degassing flow loop 116, and thereby increase the amount of $CO_2$ removed by the degasser as shown in FIGS. 3 and 7. The control unit can increase the pump rate of the vacuum pump 110, to remove the increased amount of gas being released from solution when the flow rate through the fluid pump is increased 116 which also enables the proper liquid level to be maintained in the degas vessel when the pressure within the degas vessel is reduced and causes the removal of more $CO_2$. Steps 116 and 110 can both be carried out in response to a signal showing that the $CO_2$ concentration is too high. Regardless of the action taken in response to the data received by the $CO_2$ sensor, the $CO_2$ concentration in the dialysate can be continuously monitored, as represented by arrow 120, and further adjustments to the rate of the fluid pump can be made as the $CO_2$ concentration in the dialysate changes. In the embodiments of the first, second and third aspects of the invention depicted in FIG. 10, the vacuum pump may run continuously with the exception of step 115, to draw out the $CO_2$ from the degas vessel as the $CO_2$ accumulates.

Figure 11:
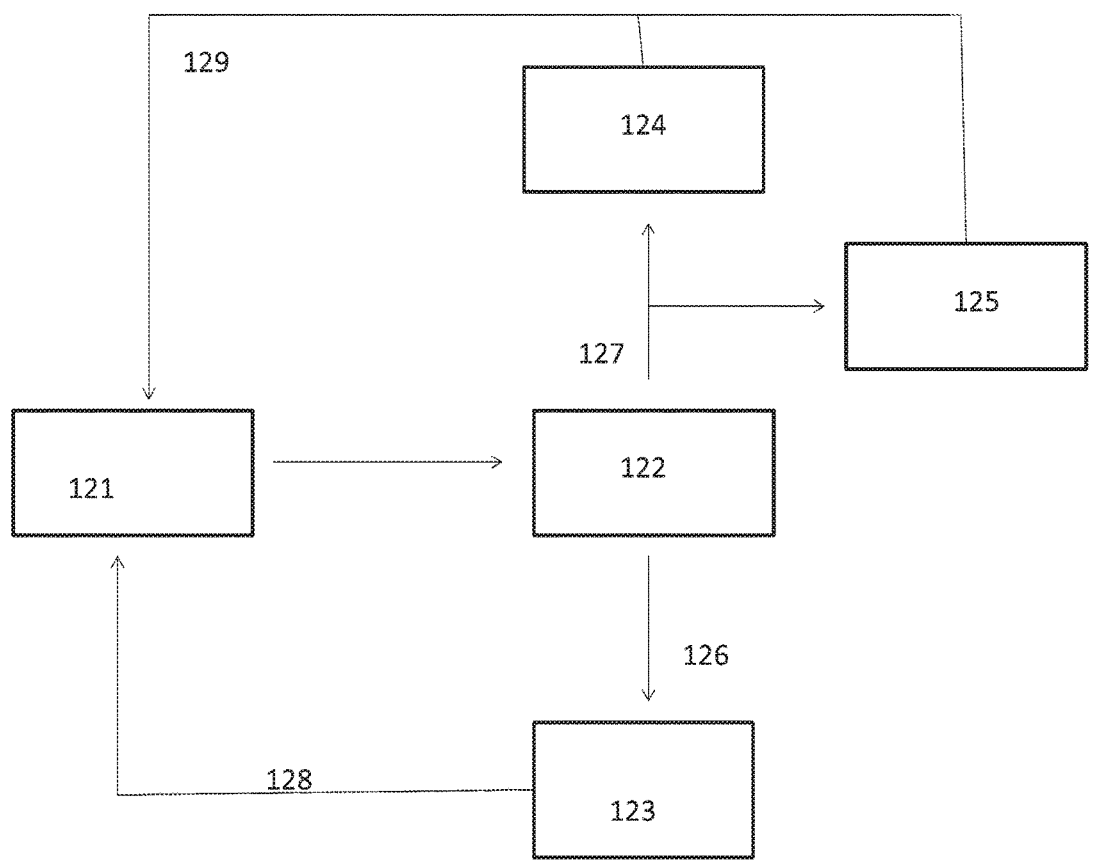
FIG. 11 is a flow diagram showing an alternative operation of the pumps in relation to the carbon dioxide present in the dialysate.

FIG. 11 shows an alternative embodiment of the first, second and third aspects of the invention to that shown in FIG. 10, where the vacuum pump and fluid pump are run alternately. The fluid pump can be operated to pull fluid through the degassing flow loop. Data is sent from the $CO_2$ sensor 121 to the control unit 122 showing the $CO_2$ concentration in the dialysate. While the $CO_2$ concentration in the dialysate is above the desired range 123, the fluid pump can be operated as explained above to remove $CO_2$ from the dialysate. The $CO_2$ concentration can be continuously monitored as the fluid pump operates, as shown by arrow 128. Once the $CO_2$ concentration has decreased into the desired range 127, the control unit can cause the fluid pump to shut off 124. Simultaneously, the vacuum pump can be turned on 125 to remove the gases that have collected in the degas vessel. While the fluid pump is shut down, the $CO_2$ concentration in the dialysate will increase, due to the fact that dialysate is not being directed through the degasser, and will be monitored as shown by arrow 129. When the $CO_2$ concentration has risen 126 to a pre-set point 123, the fluid pump can again be operated and the vacuum pump shut off.

In any embodiment of the first, second and third aspects of the invention, the control system can set initial pump rates for both the vacuum pump and fluid pump based on the initial carbon dioxide concentration in the dialysate. For example, if the initial carbon dioxide concentration in the dialysate is 415 mmHg partial pressure, the fluid pump and vacuum pump may be set to maintain an absolute pressure in the degas vessel of 100 mmHg. As shown in FIG. 3, this would allow for an outlet $CO_2$ concentration of between 50-120 mmHg partial pressure. If, during operation, the concentration of carbon dioxide were to become reduced to 117 mmHg partial pressure, the control system can alter the pump rates of the fluid pump and/or vacuum pump as described above to maintain an absolute pressure in the degas vessel of 190 mmHg. As shown in FIG. 3, this would keep the concentration of carbon dioxide at a level above 50 mmHg partial pressure.

In any embodiment of the first, second and third aspects of the invention, the degasser can be located in a fluid flow path in a position directly after the sorbent cartridge. The position of the degasser, however, is not limited to any one position. In any embodiment of the first, second and third aspects of the invention, the degassing module may be located in other positions between the sorbent cartridge and the dialyzer.

To make use of the dialysis system of the first, second and third aspects of the invention easier, the valves and pumps may be operated by a programmable controller or computer system that can be programmed to regulate flow through the pumps and valves and into and out of the reservoirs. A rotometer or turbine with optical sensor, photocell, magnetic sensor, or other flow sensing apparatus may detect the flow of fluid through any two points in the degassing system. For example, an optical fluid flow device can be provided for measuring flow wherein the device includes an optical fluid pressure measuring device having sensors positioned in any one of the flow paths between the reservoirs, in the connectors, or in the valves or valve assemblies. In any embodiment of the first, second and third aspects of the invention, the optical fluid sensors described above can be connected to an interferometer associated with an opto-electronic demodulator which has an output signal representing the differential pressure between the two sensed areas. In any embodiment of the first, second and third aspects of the invention, a flow sensing apparatus can have a flow-responsive element projecting into a fluid flow path, and a position sensor associated with the element which detects a change in position of the flow-responsive element in response to the fluid flow. The flow-responsive element can be made of a wide variety of materials having the desired properties known to those of ordinary skill in the art.

The reader is directed to FIG. 8a, which demonstrates the relationship be between the pressure in the degasser and the concentration of dissolved carbon dioxide in the fluid that has passed through the degasser, and also to FIG. 9a, which demonstrates that the carbon dioxide concentration in the fluid that has passed through the degasser remained constant in a tight range when the carbon dioxide concentration in the fluid entering the degasser was more than doubled. As illustrated in FIG. 8a and FIG. 9a, the operating pressure of the degasser can be used to control the concentration of carbon dioxide in the fluid exiting the degasser.

Figure 12:
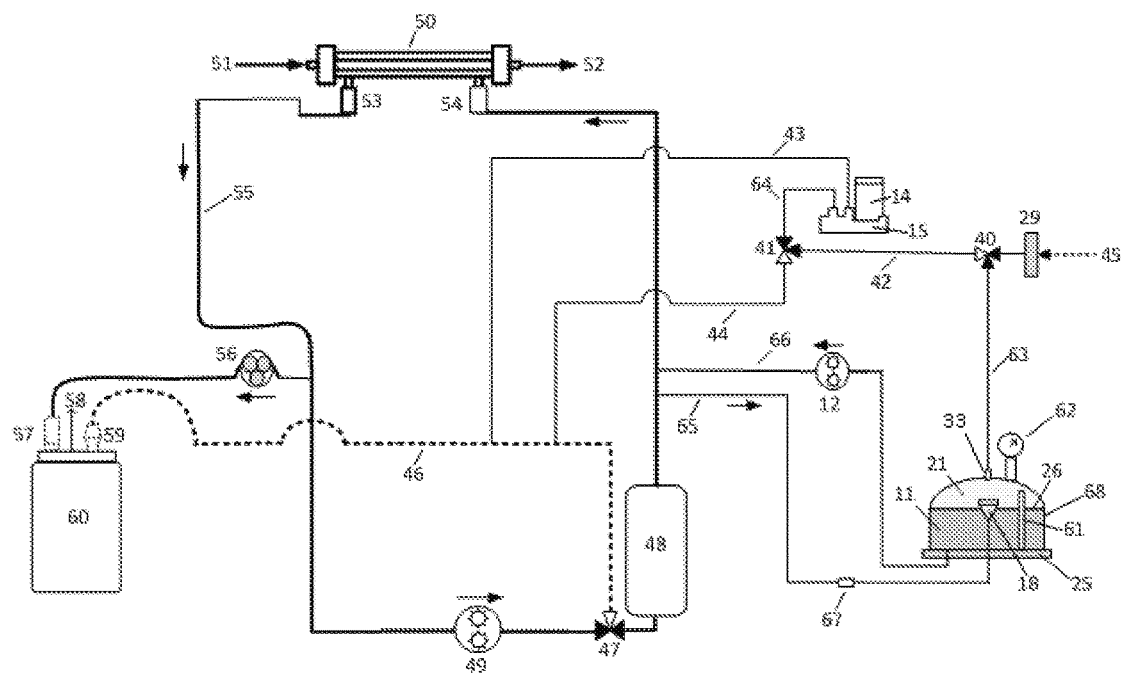
FIG. 12 is a schematic of a degassing system having a pressure sensor to measure the pressure within the degasser; and having control valves to alternately connect the vent port of the degassing vessel to an air inlet filter, a drain line for gas removal through a vacuum pump, or a dialysate flow path for recirculation of fluid.

Referring to FIG. 12, a description is provided of how the concentration of dissolved carbon dioxide in the dialysate can be controlled by controlling the operating fluid pressure in the degasser to a predetermined level. Blood enters dialyzer 50 as shown by arrow 51 and exits the dialyzer 50 as shown by arrow 52. Dialysate recirculating in dialysate flow path 55 enters the dialyzer 50 at connector 54 and exits the dialyzer 50 at connector 53 with urea that has been removed from the blood. The dialysate is pumped by dialysate pump 49 through valve 47 and through sorbent cartridge 48 where the urea is removed from the dialysate by an exchange process that results in carbon dioxide being added to the dialysate as the dialysate flows through sorbent cartridge 48. The dialysate exiting the sorbent cartridge 48 is drawn into the degassing system by action of fluid pump 12 through inlet line 65. The dialysate passes through degas flow restrictor 67 where the fluid pressure is reduced by the pressure drop that occurs as the dialysate flows through the degas flow restrictor 67. The dialysate enters degassing vessel 68 and passes through optional sprayer 18 that acts to increase the surface area of the liquid and thereby increase the rate at which the dissolved carbon dioxide is released from the fluid to the gas space 21 at the top of the degassing vessel 68. Carbon dioxide gas is collected in the gas space 21 and the degassed fluid is collected in the liquid space 11. Gas bubbles in the liquid rise to be collected in gas space 21 and the liquid exits the base 25 of degassing vessel 68 and passes through fluid pump 12 and is returned to the recirculating dialysate flow path 55 through return line 66.

The released gas can exit the degassing vessel 68 at outlet connector 33 and pass through vent line 63 to vent valve 40 through outflow line 42 to outflow valve 41. During degassing, outflow valve 41 directs the flow path to gas removal apparatus 15 through gas removal line 64. Vacuum pump 14 pulls the gas from the low pressure environment of degassing vessel 68 and pumps the gas out through degassing outlet line 43. Degassing outlet line 43 can optionally be connected to drain line 46. Connecting degassing outlet line 43 to drain line 46 muffles the noise of the gas removal pump 14 and directs any condensed water vapor to reservoir 60 through drain line 46 and connector 59. The removed gas flows out of reservoir 60 through vent 58.

Level sensor 61 can measure the liquid level 26 in degassing vessel 68. Level sensor 61 can be an ultrasonic sensor. Level sensor 61 can be an array of reed switches that detect the height of a magnetic float. Level sensor 61 can be an array of hall-effect sensors. The rate of gas removal pump 14 can be increased to increase the liquid level 26 when level sensor 61 detects that the liquid level 26 is below a predetermined level. The rate of gas removal pump 14 can be reduced when the level sensor 61 detects that the liquid level 26 is above a predetermined level. In any embodiment of the first, second and third aspects of the invention, the gas removal pump 14 can act as a check valve preventing air or liquid from returning to the degasser through degassing outlet line 43, but can allow gas outflow from the degasser through degassing outlet line 43 including when the gas removal pump is de-energized or turned off. Air can be rapidly evacuated from the dialysate flow path 55 through outlet connector 33, vent line 63, vent control valve 40, degassing outflow valve 41 and gas removal apparatus 15 and degassing outlet line 43 during priming operations when the liquid entering the dialysate flow path 55 causes the pressure to increase, forcing the air in the gas space 21 of degassing vessel 68 through outlet connector 33 when the pressure in gas space 21 is greater than atmospheric pressure.

Vent valve 40 can be switched to filter 29 and air can be drawn into the degassing vessel 68 as depicted by arrow 45 when liquid is being drained from the recirculating dialysate flow path 55 through drain valve 47 through drain line 46 and connector 59 to reservoir 60. Filter 29 can have a pore size that excludes microbes and particulate to prevent contamination of the system when air is drawn in.

During flushing, cleaning and disinfection of the dialysis system, degassing vessel 68 can be completely filled with liquid and liquid can be passed out through outlet connector 33 through vent line 63, vent control valve 40, and degassing outflow valve 41 to recirculation line 44. This flow path enables cleaning and disinfection solutions, including the non-limiting examples of hot water, heated citric acid solution, and bleach to be recirculate through the outlet connector 33, vent line 63, and vent control valve 40. In this manner microbiological contamination and biofilms can be minimize in the degassing vessel 68 and also in the flow path used to bring air into the system when liquid is being drained from the system.

In any embodiment of the first, second and third aspects of the invention, the flow restrictor 67 can have a fixed restriction, or can comprise a pressure regulator that changes the amount of flow restriction as the pumping rate of fluid pump 12 changes, such that a predetermined pressure is maintained in the dialysate exiting the restrictor across a range of operating rates of fluid pump 12. In any embodiment of the first, second and third aspects of the invention, the amount of restriction caused by flow restrictor 67 can be controlled to achieve a predetermined pressure in the fluid passing through the degasser.

Pressure sensor 62 can measure the fluid pressure in the degassing system. Pressure sensor 62 can be located on the degassing vessel and can measure the pressure in the liquid or the gas. Pressure sensor 62 can be located at any point in the degasser between the flow restrictor 67 and fluid pump 12. In any embodiment of the first, second and third aspects of the invention, the pressure measurement obtained from pressure sensor 62 can be used to adjust the restriction of flow restrictor 67 to obtain a predetermined pressure in the degassing system. In any embodiment of the first, second and third aspects of the invention, the rate of fluid pump 12 can be controlled to achieve a predetermined fluid pressure in the degassing system. The rate of fluid pump 12 can be increased to reduce the fluid pressure in the degasser if the fluid pressure measured by pressure sensor is above the predetermined pressure. The rate of fluid pump 12 can be decreased to increase the fluid pressure in the degasser if the fluid pressure measured by pressure sensor 62 is below the predetermined fluid pressure.

In FIG. 12, an alternative control scheme can be employed in any embodiment of the first, second or third aspects of the invention, wherein the pressure in the gas space 21 can be controlled by gas removal pump 14. The pressure in the gas space 21 can be measured by pressure sensor 62 and a controller can adjust the rate of gas removal pump 14 to keep the pressure in gas space 21 at a predetermined level. In this alternative control scheme, the rate of fluid pump 12 can be increased to decrease the liquid level 26 in degassing vessel 68 or the rate of fluid pump 12 can be decreased to increase the liquid level 26 in degassing vessel 68. In this scheme liquid level measurements from level sensor 61 can be used to determine whether the rate of fluid pump 12 should be increased or decreased. Those of skill in the art will note that the rate of fluid pump 12 can be maintained at a constant rate while increasing the amount of flow restriction caused by flow restrictor 67 to decrease the liquid level 26 in degassing vessel 68 or decreasing the amount of flow restriction caused by flow restrictor 67 to increase liquid level 26 in degassing vessel 68.

It will be apparent to one skilled in the art that various combinations and/or modifications and variations can be made in the dialysis system depending upon the specific needs for operation. Moreover features illustrated or described as being part of an aspect of the invention can be included in the aspect of the invention, either alone or in combination.

We claim:

1. A degassing vessel for use in dialysis; comprising:
   a fluid inlet in the degassing vessel fluidly connected to a flow restriction;
   a fluid outlet in the degassing vessel for fluid connection to a fluid pump downstream of the degassing vessel;
   a gas outlet for connection to a vacuum pump;
   one or more sensors contacting the degassed fluid downstream of the degassing vessel;
   a degas sprayer; wherein fluid entering the degassing vessel through the fluid inlet passes through the degas sprayer;
   and a control system, the control system programmed to control a pressure in the degassing vessel based on an amount of gas to be removed from a fluid entering the degassing vessel.

2. The degassing vessel of claim 1, further comprising a lower level sensor and upper level sensor in electronic communication with the control system.

3. The degassing vessel of claim 1, wherein the control system is programmed to adjust a pump rate of the fluid pump and a pump rate of the vacuum pump to maintain a desired fluid level in the degassing vessel.

4. The degassing vessel of claim 1, wherein the control system is programmed to adjust a pump rate of the fluid pump and a pump rate of the vacuum pump in response to signals received from a sensor to remove more or less of a dissolved gas from a dialysate.

5. The degassing vessel of claim 1, wherein the control system is programmed to adjust a pump rate of the fluid pump and a pump rate of the vacuum pump in response to signals received from a sensor to deliver more or less of a gas to a main dialysate flow path.

6. The degassing vessel of claim 1, wherein the flow restriction is selected from the group consisting of orifices, venturis, spray nozzles, a narrowing, pinch valves, gate valves, variable orifice valves, a pressure regulator, and combinations thereof.

7. The degassing vessel of claim 1, further comprising a pressure sensor configured to determine a fluid pressure in the degassing vessel.

8. The degassing vessel of claim 1, further comprising one or more sensors in the degassing vessel wherein the one or more sensors are configured to determine a fluid level in the degassing vessel.

9. The degassing vessel of claim 1, further comprising an ultrasonic sensor or mechanical float determining a fluid level in the degassing vessel.

10. The degassing vessel of claim 1, further comprising a carbon dioxide sensor positioned to detect carbon dioxide at the fluid outlet of the degassing vessel.

11. The degassing vessel of claim 8, wherein the one or more sensors in the degassing vessel comprise an upper level sensor and a lower level sensor in the degassing vessel; wherein the upper level sensor detects whether the fluid level in the degassing vessel is above a first pre-set point; and wherein the lower level sensor detects whether the fluid level in the degassing vessel is below a second pre-set point.

12. The degassing vessel of claim 1, further comprising:
    an overflow float in the degassing vessel, the overflow float being of a lower density than water; and
    a mechanical vent valve placed on the degassing vessel at the gas outlet such that if a fluid level in the degassing vessel is above a pre-set point, the overflow float will cover the mechanical vent valve and block fluid from passing through the mechanical vent valve.

13. The degassing vessel of claim 1, further comprising a nucleation chamber;
    wherein fluid entering the degassing vessel through the fluid inlet passes through the nucleation chamber.

14. The degassing vessel of claim 1, wherein the control system is programmed to adjust the pressure in the degassing vessel to provide a carbon dioxide concentration in a fluid after passing through the degasser having any of 50 and 200 mmHg partial pressure, 50 and 120 mmHg partial pressure, 50 and 80 mmHg partial pressure, 70 and 100 mmHg partial pressure, 80 and 120 mmHg partial pressure, 50 and 200 mmHg partial pressure, or 100 and 200 mmHg partial pressure.

15. The degassing vessel of claim 1, further comprising a sensor attached to the fluid pump or vacuum pump to monitor performance of the fluid pump or vacuum pump.

* * * * *